US006914052B2

(12) United States Patent
McLaughlin et al.

(10) Patent No.: US 6,914,052 B2
(45) Date of Patent: Jul. 5, 2005

(54) SELECTIVE ANTI-VIRAL NUCLEOSIDE CHAIN TERMINATORS

(75) Inventors: Larry W. McLaughlin, Dover, MA (US); Andrew W. Fraley, WestNewton, MA (US); DongLi Chen, Chestnut Hill, MA (US); Tao Lan, Somerville, MA (US)

(73) Assignee: The Trustees of Boston College, Chestnut Hill, MA (US)

( * ) Notice: Subject to any disclaimer, the term of this patent is extended or adjusted under 35 U.S.C. 154(b) by 206 days.

(21) Appl. No.: 10/097,672

(22) Filed: Mar. 13, 2002

(65) Prior Publication Data

US 2003/0100759 A1 May 29, 2003

Related U.S. Application Data

(60) Provisional application No. 60/276,015, filed on Mar. 15, 2001, provisional application No. 60/317,026, filed on Sep. 4, 2001, and provisional application No. 60/337,854, filed on Dec. 5, 2001.

(51) Int. Cl.[7] .................. A61K 31/70; C07H 19/048
(52) U.S. Cl. .................. 514/43; 514/81; 514/85; 514/89; 536/29.2; 544/124; 544/242; 544/243; 544/278
(58) Field of Search .................. 514/43, 45, 81, 514/85, 89; 536/27.13, 27.14, 27.2, 29.2; 544/242, 243, 278, 124

(56) References Cited

U.S. PATENT DOCUMENTS

| 4,092,472 | A |   | 5/1978  | Townsend et al. .......... 536/29.2 |
| 5,627,160 | A |   | 5/1997  | Lin et al. .................. 514/49 |
| 6,117,849 | A |   | 9/2000  | Zimmermann et al. ....... 514/45 |
| 6,159,951 | A | * | 12/2000 | Karpeisky et al. ............ 514/45 |
| 6,232,300 | B1 |  | 5/2001  | Schinazi et al. ............. 514/49 |
| 6,248,878 | B1 | * | 6/2001 | Matulic-Adamic et al. ...... 536/29.2 |
| 6,312,892 | B1 | * | 11/2001 | Barany et al. ................. 435/6 |
| 6,447,998 | B1 | * | 9/2002 | Froehler et al. ............... 435/6 |
| 6,495,672 | B1 | * | 12/2002 | Froehler et al. ............ 536/23.1 |
| 6,576,453 | B2 | * | 6/2003 | Barany et al. .............. 435/193 |
| 2003/0082545 | A1 | * | 5/2003 | Barany et al. ................. 435/6 |

FOREIGN PATENT DOCUMENTS

| EP | 0 038 569 | 10/1981 |
| EP | 0 043 722 | 1/1982 |
| EP | 0 236 935 | 9/1987 |
| EP | 0 544 010 | 6/1993 |
| JP | 01-066197 | 3/1989 |
| WO | WO 90/11081 | 10/1990 |
| WO | WO 94/01117 | 1/1994 |
| WO | WO 94/18971 | 9/1994 |
| WO | W O 97/41140 A1 | * 11/1997 |

OTHER PUBLICATIONS

Searls et al., "Nucleoside Analogue Substitutions in the Trinucleotide DNA Template Recognition Sequence 3'–(CTG)–5' and Their Effects on the Activity of Bacteriophage T7 Primase," *Biochemistry*, 39(15), 4375–4382 (Apr. 18, 2000).*

Hildbrand et al. (I), "5–Substituted 2–Aminopyridine C–Nucleosides as Protonated Cytidine Equivalents: Increasing Efficiency and Specificity in DNA Triple–Helix Formation," *J. American Chemical Society*, 119(24), 5499–5511 (Jun. 18, 1997).*

Bates et al., "Efficient Triple Helix Formation by Oligonucleotides Containing α– or β–2–amino–5–(2–deoxy–D–ribofuranosyl)pyridine Residues," *Nucleic Acids Research*, 24(21), 4176–4184 (Nov. 1, 1996).*

Hildbrand et al. (II), Enhancing DNA Triple Helix Stability at Neutral pH by the Use of Oligonucleotides Containing a More Basic Deoxycyidine Analog, *Angewandte Chemie, Intl. Ed.*, 35(17), 1968–1970 (1996); see also *Chemical Abstracts*, 126(1), p. 943, Abstr. No. 8456u (Jan. 6, 1997).*

Hsieh et al., "Synthesis of Two Pyridine C–Nucleosides as 'Deletion–Modified' Analogues of dT and dC," *Journal of Organic Chemistry*, 60(16), 5356–5359 (Aug. 11, 1995).*

Chen et al., "Use of $pK_a$ Differences to Enhance the Formation of Base Triplets Involving C–G and G–C Base Pairs," *Journal of Organic Chemistry*, 65(22), 7468–7474 (Nov. 3, 2000).*

Minakawa et al., "Nucleosides and Nucleotides. 184. Synthesis and Conformational Investigation of Anti–Fixed 3–Deaza–3–halopurine Ribonucleosides," *Journal of Organic Chemistry*, 64(19), 7158–7172 (Sep. 17, 1999).*

Aoyagi et al. (I), "Nucleosides and Nucleotides. 115. Synthesis of 3–Alkyl–3–deazainosines v ia Palladium–Catalyzed Intramolecular Cyclization: A New Conformational Lock with the Alkyl Group at the 3–Position of 2–Deazainosine in Anti–Conformation," *Tetrahedron Letters*, 34(1), 103–106 (Jan. 1, 1993).*

(Continued)

*Primary Examiner*—James O. Wilson
*Assistant Examiner*—L. E. Crane, Esq.
(74) *Attorney, Agent, or Firm*—Palmer & Dodge LLP

(57) ABSTRACT

The present invention relates to dideoxynucleoside analog compounds containing a dideoxy ribofuranosyl moiety that exhibit selective anti-viral activity coupled with substantially low toxicity toward the host cells. In particular, the compounds according to the present invention show potent inhibition of the replication of the human immunodeficiency virus (HIV), while remaining substantially inert toward host cell DNA. Compounds according to the present invention exhibit primary utility as agents for inhibiting the growth or replication of retroviruses, particularly HIV. The compounds of the invention comprise a (2,3'-dideoxy-β-ribofuranosyl) ring coupled to a heterocyclic nucleobase that lacks an "O2 carbonyl", that enables them to selectively react with and inhibit viral reverse transcriptase, while remaining substantially unreactive toward human DNA polymerases.

17 Claims, 13 Drawing Sheets

OTHER PUBLICATIONS

Aoyagi et al. (II), "Synthesis of Imidazo[4,5–e][1,4]diazepine and 3–Substituted 3–Deazapurine Nucleosides from 1–Substituted Inosines," *18th Symposium on Nucleic Acids Chemistry, Nucleic Acids Symposium Series*, 25, 57–58 (Oct. 29–31, 1991); see also *Chemical Abstracts, 117*(25), Abstr. No. 251690d(Dec. 21, 1992).*

Yamagata et al., "Conformation of 3–Substituted Purine Nucleosides Studied by X–Ray Crystallography and Theoretical Calculations," *Nucleosides & Nucleotides*, 13(6&7), 1327–1335 (1994); see also*Chemical Abstracts, 121*(13), p. 1073, Abstr. No. 158083f (Sep. 26, 1994);.*

Orr et al., "DNA Chain Termination Activity and Inhibition of Human Immunodeficiency Virus Reverse Transcriptase by Carbocyclic 2',3'–Didehydro–2'.3'–dideoxyguanosine Triphosphate," *Journal of Biological Chemistry*, 267(6), 4177–4182 (Feb. 25, 1992).*

Serafinowski, et al.; "Synthesis and Antiviral Activity of Some New S–Adenosyl–L–Homocysteine Derivatives"; *J. Med. Chem.*; (1992); 35: 4576–4583.

Aoyagi, et al.; "Nucleosides and Nucleotides. 115. Synthesis of 3–Alkyl–3–Deazainosines via Palladium–Catalyzed Intramolecular Cyclization: A New Conformational Lock with the Alkyl Group at the 3–Position of the 3–Deazai nosine in Anti–Conformation"; *Tetrahedron Letters*; (1993); 34: 1, 103–106.

Hildbrand, et al.; "Synthesis of Carbocyclic C–Nucleosides Containing Nonnatural Pyrimidine Bases"; *Helvetica Chimica Acta*; (1996); 79: 3, 702–709.

Chen, et al.; "Use of $PK_a$ Differences To Enhance the Formation of Base Triplets Involving C–G amd G–C Base Pairs"; *J. Org. Chem.*; (2000); 65: 7468–7474.: ACS web publ. on Sep. 15, 2000.

Copy of International Search Report; International Application No.: PCT/US02/07447; mailed Oct. 2, 2002.

Stolze, et al.; "Synthesis of 3'–Sugar– and Base–Modified Nucleotides and Their Application as Potent Chain Terminators in DNA Sequencing"; (1999); *Helvetica Chimica. ACTA*; vol. 82, pp. 1311–1323.

Guo, et al.; "Inhibition of DNA polymerase reactions by pyrimidine nucleotide analogues lacking the 2–keto group"; (1998); *Nucleic Acids Research*; vol. 26, No. 8, pp. 1863–1869.

* cited by examiner

Incorporation of a nucleoside triphosphate into a growing primer/template complex

| Position | Preferred subsitutent | Other substituents |
|---|---|---|
| $R_1$ | -H | -F, -Cl, -Br, -I, -CH$_3$, -CF$_3$, |
| $R_2$ | -NH$_2$ | -NHR with R = -CH$_3$, -CH$_2$CH$_3$, |
| $R_3$ | -H | -CH$_3$, -CH$_2$CH$_3$, -CH$_2$C≡CH |
| $R_4$ | -H | -CH$_3$ |
| $R_5$ | -H | -F, -OH, |
| $R_6$ | -H | -F, -OH |
| $R_7$ | -H | -F, -OH, -N$_3$ |
| $R_8$ | -H | -F, -OH |
| $R_9$ | -OH | -P(O)(OH)$_2$, -CH$_2$P(O)(OH)$_2$, -OP(O)(OH)$_2$, -OP(O)(OR)2 R = hydroxyl protecting group |
| $R_{10}$ | -O- | -CH$_2$-, -S- |

| Position | Preferred substituent | Other substituents |
|---|---|---|
| $R_1$ | -H | -F, -Cl, -Br, -I, -CH$_3$, -CF$_3$, |
| $R_2$ | =O | =S, =NH, =Se |
| $R_3$ | -CH$_3$ | -H |
| $R_4$ | -H | -CH$_3$ |
| $R_5$ | -H | -F, -OH, |
| $R_6$ | -H | -F, -OH |
| $R_7$ | -H | -F, -OH, -N$_3$ |
| $R_8$ | -H | -F, -OH |
| $R_9$ | -OH | -P(O)(OH)$_2$, -CH$_2$P(O)(OH)$_2$, -OP(O)(OH)$_2$, -OP(O)(OR)2 R = hydroxyl protecting group |
| $R_{10}$ | -O- | -CH$_2$-, -S- |

(g)          (h)

| Position | Preferred substituent | Possible substituents |
|---|---|---|
| $R_1$ | -H | -F, -Cl, -Br, -I, -CH$_3$, -CF$_3$, |
| $R_2$ | -NH$_2$ | -NHR with R = -CH$_3$, -CH$_2$CH$_3$, |
| $R_3$ | -H | -CH$_3$, -CH2CH3, -CH2C≡CH |
| $R_4$ | -H | -CH$_3$ |
| $R_5$ | -H | -F, -OH, |
| $R_6$ | -H | -F, -OH |
| $R_9$ | -OH | -P(O)(OH)$_2$, -CH$_2$P(O)(OH)$_2$, -OP(O)(OH)$_2$, -OP(O)(OR)2  R = hydroxyl protecting group |
| $R_{10}$ | -O- | -CH$_2$-, -S- |

| Position | Preferred substituent | Possible substituents |
|---|---|---|
| $R_1$ | -H | -F, -Cl, -Br, -I, -CH$_3$, -CF$_3$ |
| $R_2$ | =O | =S, =NH, =Se |
| $R_3$ | -CH$_3$ | -H |
| $R_4$ | -H | -CH$_3$ |
| $R_5$ | -H | -F, -OH |
| $R_6$ | -H | -F, -OH |
| $R_7$ | -H | -F, -OH, -N$_3$ |
| $R_8$ | -H | -F, -OH |
| $R_9$ | -OH | -P(O)(OH)$_2$, -CH$_2$P(O)(OH)$_2$, -OP(O)(OH)$_2$, -OP(O)(OR)2<br>R = hydroxyl protecting group |
| $R_{10}$ | -O- | -CH$_2$-, -S- |

| Position | Preferred subsitutent | Possible substituents |
|---|---|---|
| $R_1$ | -H | -F, -Cl, -Br, -I, -CH$_3$, -CF$_3$, |
| $R_2$ | -NH$_2$ | -NHR with R = -CH$_3$, -CH$_2$CH$_3$, |
| $R_3$ | -H | -CH$_3$ |
| $R_5$ | -H | -F, -OH, |
| $R_6$ | -H | -F, -OH |
| $R_7$ | -H | -F, -OH, -N$_3$ |
| $R_8$ | -H | -F, -OH |
| $R_9$ | -OH | -P(O)(OH)$_2$, -CH$_2$P(O)(OH)$_2$, -OP(O)(OH)$_2$, -OP(O)(OR)2  R = hydroxyl protecting group |
| $R_{10}$ | -O- | -CH$_2$-, -S- |

(i)  (j)  (k)  (l)

| Position | Preferred subsitutent | Possible substituents |
|---|---|---|
| $R_1$ | -H | -F, -Cl, -Br, -I, -_3_, -CF$_3$ |
| $R_2$ | -NH$_2$ | -NHR with R = -CH$_3$, -CH$_2$CH$_3$ |
| $R_3$ | -H | -CH$_3$ |
| $R_5$ | -H | -F, -OH, |
| $R_6$ | -H | -F, -OH |
| $R_7$ | -H | -F, -OH, -N$_3$ |
| $R_8$ | -H | -F, -OH |
| $R_9$ | -OH | -P(O)(OH)$_2$, -CH$_2$P(O)(OH)$_2$, -OP(O)(OH)$_2$, -OP(O)(OR)2<br>R = hydroxyl protecting group |
| $R_{10}$ | -O- | -CH$_2$-, -S- |

| Position | | Substituents |
|---|---|---|
| $R_1$ | -H | -F, -Cl, -Br, -I, -CH$_3$, -CF$_3$, |
| $R_2$ | -NH$_2$ | -NHR with R = -CH$_3$, -CH$_2$CH$_3$, |
| $R_3$ | -H | -CH$_3$, -CH2CH3, -CH2C≡CH |
| $R_4$ | -H | -CH$_3$ |
| $R_5$ | -H | -F, -OH, |
| $R_6$ | -H | -F, -OH |
| $R_7$ | -H | -F, -OH, -N$_3$ |
| $R_8$ | -H | -F, -OH |
| $R_9$ | -OH | -P(O)(OH)$_2$, -CH$_2$P(O)(OH)$_2$, -OP(O)(OH)$_2$, -OP(O)(OR)2<br>R = hydroxyl protecting group |
| $R_{10}$ | -O- | -CH$_2$-, -S- |

(d) (e) (f)

| Position | | Substituents |
|---|---|---|
| $R_1$ | -H | -F, -Cl, -Br, -I, -CH$_3$, -CF$_3$, |
| $R_2$ | =O | =S, =NH, =Se |
| $R_3$ | -H | -CH$_3$, -CH2CH3, -CH2C≡CH |
| $R_4$ | -H | -CH$_3$ |
| $R_5$ | -H | -F, -OH, |
| $R_6$ | -H | -F, -OH |
| $R_7$ | -H | -F, -OH, -N$_3$ |
| $R_8$ | -H | -F, -OH |
| $R_9$ | -OH | -P(O)(OH)$_2$, -CH$_2$P(O)(OH)$_2$, -OP(O)(OH)$_2$, -OP(O)(OR)2 |
| | | R = hydroxyl protecting group |
| $R_{10}$ | -O- | -CH$_2$-, -S- |

SELECTIVE ANTI-VIRAL NUCLEOSIDE CHAIN TERMINATORS

This application claims priority to U.S. Provisional Application Ser. No. 60/276,015 filed on Mar. 15, 2001, U.S. Provisional Application Ser. No. 60/317,026 filed on Sep. 4, 2001 and U.S. Provisional Application Ser. No. 60/337,854 filed on Dec. 5, 2001, all of the foregoing are incorporated herein by reference.

STATEMENT AS TO FEDERALLY FUNDED RESEARCH

The present invention was made with partial support from the National Science Foundation Grant No. MCB 0077667. The United States Government retains certain rights to the invention.

FIELD OF THE INVENTION

This invention relates to biologically active dideoxy nucleoside analogs and includes their physiologically acceptable derivatives and salts. Compounds of the invention exhibit selective activity against retroviruses, and in particular against human immunodeficiency virus (HIV). The present invention also relates to pharmaceutical compositions containing these compounds and to methods of inhibiting the replication of HIV virus while remaining substantially chemically inactive to mammalian DNA in the host cell, as well as treating HIV viral infections in mammals, particularly in humans.

BACKGROUND OF THE INVENTION

Retroviruses are a class of viruses having a single-stranded RNA genome that reproduce in a host organism by generating a DNA copy of its genome by action of a virally coded RNA-directed DNA polymerase, reverse transcriptase. Reverse transcriptase can construct double-stranded DNA molecules from the single stranded RNA of the viral genome. The most notorious retrovirus is the human immunodeficiency virus (HIV), which is responsible for the generally fatal disease, acquired immune deficiency syndrome (AIDS). Although the disease itself has been studied greatly, it has been treated only with limited success.

A number of nucleosides have been utilized in the treatment of HIV infections. 3'-azido-3'-deoxythymidine (AZT) is a prime example, although its ability to completely reverse the progress of the disease remains unconfirmed. A number of 2',3'-dideoxynucleoside analogs have also been reported to exhibit activity against HIV, including 3'-deoxy-2',3'-didehydrothymidine (d4T), the carbocyclic analog of 2',3'-dideoxy-2',3'-didehydroguanosine (Carbovir), 2',3'-dideoxycytidine (ddC), 3'-azido-2',3'-dideoxyguanosine (AZG), 2',3'-dideoxyinosine (ddI), 2',3'-dideoxy-2',3'-didehydrocytidine (d4C), 3'-fluoro-2',3'-dideoxyadenosine, 3'-fluoro-3'-deoxythymidine and 3'-azido-2',3'-dideoxyuridine. Some of these analogs, including ddC, are presently used as anti-HIV agents. Among the dideoxynucleosides, ddC has been shown to be a potent inhibitor of HIV.

Although research has concentrated on developing an effective treatment for AIDS and certain potent anti-HIV nucleoside analogs have been synthesized and characterized, an ideal drug has not been found. The major limitation in providing an optimized drug for treatment against retroviral infections, including HIV, remains the inability to provide the necessary anti-viral activity while maintaining minimal toxicity to the host cell (mammalian DNA).

The viral replication process is believed to be an important event in the progress of AIDS. It is also believed that the enzyme reverse transcriptase plays an essential role in the replication and life cycle of HIV, and consequently, in furthering the progress of the disease. The development of potential drugs for AIDS have therefore attempted to target this enzyme, especially because of it is absent in the uninfected host cell.

Anti-retroviral nucleoside derivative compounds such as azidothymidine (AZT), dideoxyinosine (ddI) and dideoxycytidine (ddC) function by inhibiting the activity of HIV reverse transcriptase. The mode of action for such compounds primarily requires their conversion to the corresponding 5'-triphosphates, thereby enabling them to function as substrates for reverse transcriptase. Upon incorporation of such chain terminating nucleoside triphosphates, DNA synthesis of the HIV cDNA genome is terminated, thus inhibiting replication by the virus. A common problem with chain terminating nucleosides is that they exhibit significant toxicity toward non-infected healthy cells. This is presumably due to the fact that they also function as chain terminators for human DNA polymerases and therefore, interfere with normal DNA replication. The introduction of an azido functionality at the C3'-position of the furanosyl ring in AZT provides some discrimination, such that it is not accepted as well by human DNA polymerases. Nevertheless, AZT is one of the most effective anti-HIV compounds presently in clinical use.

SUMMARY OF THE INVENTION

The present invention relates to synthetic nucleoside analogs and derivatives thereof that selectively exhibit potent anti-viral activity (in particular, anti-HIV activity) while remaining inert towards mammalian DNA polymerase, thereby resulting in significantly reduced toxicity to the host cell. In contrast to the prior art compounds, the nucleoside analogs and derivatives of the present invention represent a viable therapeutic approach to retrovirus infections, particularly for the inhibition of HIV and the treatment of AIDS. Compounds of the present invention can be used to inhibit the growth or replication of HIV or other retroviruses e.g. human T-lymphotropic virus type III (HTLV III), lymphadenopathy-associated virus (LAV), as well as Hepatitis B virus (HBV).

In one aspect, the present invention relates to nucleoside and nucleotide analog compounds that are capable of selectively reacting with viral RNA, while remaining substantially inert and unreactive towards mammalian DNA. More particularly, the present invention relates to nucleoside and nucleotide analog compounds that are capable of (i) exhibiting differential reactivity towards human polymerases α, β and γ relative to reverse transcriptase with respect to their ability to be viable substrates for the enzymes; and (ii) effecting selective chain termination of the DNA replication process initiated by reverse transcriptase, thereby resulting in the inability of the virus to replicate in the infected host without terminating chain replication by human DNA polymerases. The compounds of the present invention, therefore, do not interfere with processes initiated by human DNA polymerases, thereby rendering them substantially non-toxic compared to presently known nucleoside analog reverse transcriptase inhibitors.

The nucleoside analog compounds of the present invention comprise a combination of two important structural attributes that enable them to exhibit selectivity in their ability to react with viral reverse transcriptase but not with human polymerases: (1) absence of the 3'-hydroxyl group in the ribofuranosyl ring; and (2) absence of an O2-carbonyl group (pyrimidine analogs) or the N3-nitrogen (purine analogs) from the heterocyclic aromatic ring (i.e. the nucleobase portion of the compound). For the pyrimidine analogs, the Ni-nitrogen is also replaced by carbon in order to maintain correct base pair complementarity.

The absence of the 3'-hydroxyl group in the ribofuranosyl ring is an important structural feature in the compounds of the invention that is key to their ability to effect efficient termination of DNA polymer synthesis mediated by reverse transcriptase. Although such chain termination does not distinguish between enzyme type (it occurs both for the host processes as well as for the viral process), the presence of the altered heterocyclic nucleobase results in selective incorporation of the corresponding 2',3'-dideoxy derivative by the viral-mediated process without affecting the processes initiated by human DNA polymerases α, β, or γ. Specifically, the absence of the O2 carbonyl in the nucleobase portion of the compounds prevent them from functioning as viable substrates for DNA polymerase, thereby rendering them chemically inert to host cell DNA. Stated another way, the absence of the 3'-hydroxyl group in the ribofuranosyl ring promotes chain termination of reverse transcriptase, and the absence of the O2 carbonyl group (or N3-nitrogen) in the nucleobase promotes selectivity between reverse transcriptase and host DNA polymerase.

In one aspect, the nucleoside analog compounds of the present invention comprise deoxy derivatives of cytosine and thymine, coupled to a furanosyl carbohydrate or derivative thereof and their corresponding nucleotide analogs which further comprise a triphosphate substituent. In another aspect, the present invention pertains to triphosphate ribofuranosyl or related carbohydrate derivatives of pyridine, pyrimidine, azabenzimidazole and purine compounds wherein the 3'-hydroxyl group in the furanosyl ring is absent. Compounds belonging to this class have been found to be highly discriminating towards different enzyme types; they are viable substrates for the less selective viral reverse transcriptase, but essentially non-viable substrates for the more selective human DNA polymerases, due to the absence of the O2-carbonyl group from the heterocyclic aromatic ring.

The compounds of the present invention are useful for inhibiting the activity of reverse transcriptase. Thus, they are useful therapeutically as anti-viral drugs as well as in diagnostic applications. The compounds of the invention can also be used alone or in combination with other modified nucleosides and/or naturally occurring nucleosides to prepare oligonucleotides which can be used, for example, as probes or primers in diagnostic applications.

The therapeutic aspect of the present invention relates to methods for treating retroviral infections, including HIV infections in mammals, particularly in humans. The methods of the invention for the treatment of retroviral infections comprise administering the anti-viral nucleoside compounds of the invention in effective amounts sufficient to inhibit the growth or replication of such viruses in the animal or human being treated.

Pharmaceutical compositions based on the compounds of the invention comprise the nucleoside analog compounds in a therapeutically effective concentration for treating a viral infection, particularly HIV infection, optionally in combination with pharmaceutically acceptable additives, carriers or excipients. Additionally, the nucleoside compounds of the invention, in pharmaceutical dosage form, may also be used as prophylactic agents for inhibiting the growth or replication of retroviruses. Such agents are particularly effective as anti-HIV agents.

While not being limited by way of theory, it is believed that the compounds of the present invention induce their inhibitory effect on replication of viruses, particularly HIV, by selectively reacting with and inhibiting the activity of enzymes responsible for virus replication, such as reverse transcriptase, while remaining chemically unreactive towards mammalian DNA polymerases.

The compounds according to the present invention are produced by synthetic methods and functional group transformations that are readily known to those of ordinary skill in the art; preferred synthetic processes are described in the Examples herein.

DETAILED DESCRIPTION OF THE INVENTION

Figure 1:
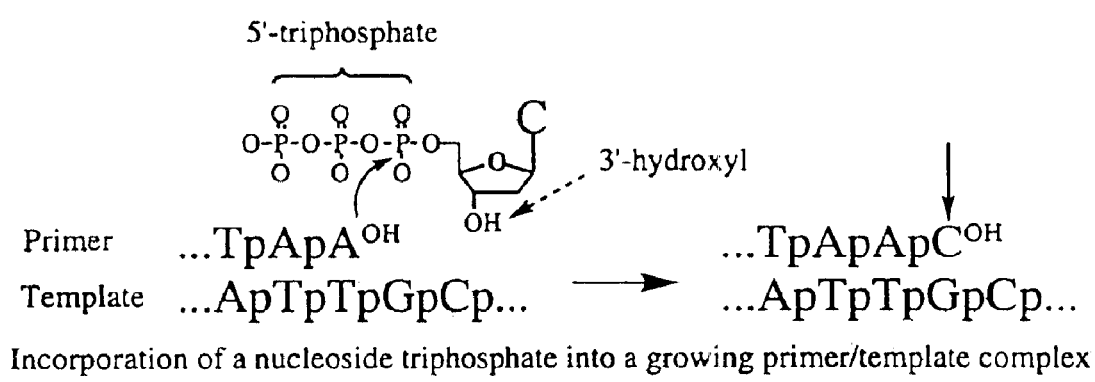
FIG. 1 shows the incorporation of a nucleoside triphosphate into a growing primer/template complex

The following terms and definitions are used throughout the specification to describe the present invention.

The numbering system used in the following descriptions is that standard for common pyrimidine and purine nucleosides even though changing the heteroatom nature of the heterocycles—particularly for the pyrimidines—would require changes in the nomenclature to correctly describe positions in the heterocyclic ring. In the experimental synthesis descriptions the correct IUPAC nomenclature has been used. Thus, the compound Ia is the 2',3'-dideoxynucleoside known as ddC. In the standard nomenclature for common pyrimidine nucleosides, the carbonyl of the ring is the O2-carbonyl designating its attachment to the C2-carbon of the heterocycle Ia. The N1-nitrogen is the site of attachment of the 2',3'-dideoxycarbohydrate ring. One of the analogs described in this invention is illustrated by structure Ib. This derivative is described as a pyrimidine analog with the O2-carbonyl deleted and the N1-nitrogen replaced by carbon so that the structure can readily be related to that containing the corresponding natural heterocycle (Ia). But in fact, changes in the heteroatom character of the heterocycle require, according to the rules of nomenclature, that the remaining ring nitrogen of structure Ib be designated as the 1-position. The amino group of ddC (Ia) is attached to the C4-carbon, but in the analog it is formally attached to the carbon at the C2-position. Similarly, the atom that links the heterocycle to the carbohydrate ring in ddC is the nitrogen at position 1, in the analog this atom is a carbon, and is now, by virtue of the vagaries of the naming rules, located at position 5. Therefore for the description of the materials of the invention we note positional differences according to the standard pyrimidine nucleoside numbering positions (Ia), while in the synthetic descriptions the formal IUPAC nomenclature is used. The compound Ib then formally becomes 2-amino-5-(2',3'-dideoxy-D-ribofuranosyl)-pyridine.

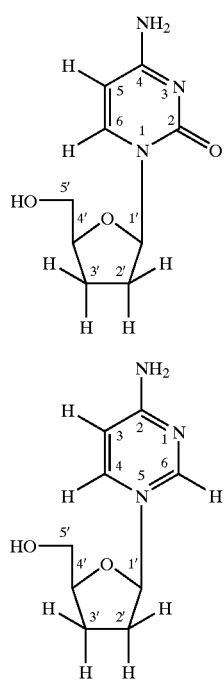

The term "deoxy" refers to describe ribofuranosyl moieties that contain a hydrogen in place of a hydroxyl group in the 2' positions of the sugar in the present compounds.

The term "dideoxy" refers to describe ribofuranosyl moieties that contain hydrogens in place of hydroxyl groups in the 2' and 3' positions of the sugar in the present compounds.

The term "didehydro" refers to describe ribofuranosyl moieties that contain a double bond. For example 2'3'-carbons of the sugar in the present compounds.

The term "O2 carbonyl" refers to a carbonyl group on the C-2 carbon atom in the natural pyrimidine nucleosides and "N3-nitrogen" refers to the nitrogen at the 3-position in the purine rings, of the present compounds.

The term "inhibitory effective concentration" or "inhibitory effective amount" as used herein refers to concentrations or amounts of compounds according to the present invention which substantially or appreciably inhibit the growth or replication of susceptible viruses, including HIV.

The term "therapeutic effective amount" as used herein refers to concentrations or amounts at which compounds according to the present invention are therapeutically effective in treating retroviral infections, and in particular, HIV infections in humans.

The term "L-conformer" and "D-conformer" as used herein refer to stereochemical configurations of the dideoxyribofuranosyl moiety in compounds according to the present invention.

The present invention is based on the discovery that certain dideoxynucleoside analogs which comprise a dideoxy ribofuranosyl moiety having a pyridine, pyrimidine or purine derivative as a substituent in which the "O2" carbonyl group or the "N3" nitrogen is absent exhibit selective activity against retroviruses, particularly against HIV, while remaining relatively inert towards mammalian DNA polymerases. In particular, the compounds according to the present invention show potent inhibition of the replication of the viruses, combined with low toxicity to the host cells (i.e., animal or human tissue).

Unlike bacterial DNA polymerases, human DNA polymerases will completely avoid the use of pyrimidine-like triphosphate analogs lacking the "O2-carbonyl" as substrates, while reverse transcriptase is able to use them as viable substrates. The absence of the O2-carbonyl in these triphosphate analogs ensures that the formation of the critical hydrogen bond that stabilizes the incoming triphosphate in the correct position during DNA synthesis is precluded, thereby rendering the present nucleotides non-viable as substrates for human DNA polymerases. Reverse transcriptase on the other hand, being a less specific enzyme, is still able use such triphosphate analogs as substrates. The differential ability of triphosphate analog compounds of the present invention to function as viable substrates only towards reverse transcriptase provides a class of potent inhibitors for processes initiated by reverse transcriptase that remain substantially inert and non-toxic to the normal DNA replication processes in mammalian cells.

The present invention comprises novel nucleoside and nucleotide analog compounds containing a base residue that is discriminated against by human DNA polymerase but is accepted by HIV reverse transcriptase. The selectivity is achieved by elimination of the O2-carbonyl substituent from the pyrimidine-like nucleotide analog or the N3-nitrogen from the purine-like nucleotide analog (as well as converting the Ni-nitrogen to a carbon to maintain base pairing complementarity), thereby precluding interaction with human DNA polymerase. Another key attribute of the compounds of the present invention is the absence of a hydroxyl substituent in the 3' position of the furanosyl ring of the nucleoside segment, thereby effecting chain termination of the HIV reverse transcriptase primer. Therefore, the combination of these attributes endows the present compounds with the ability to affect selective termination of DNA polymerization mediated by reverse transcriptase.

The fundamental chemistry involved in the elongation of the primer is illustrated in FIG. 1. The 3'-hydroxyl of the terminal residue of the primer attacks the 5'-triphosphate of the incoming dNTP derivative forming the phosphodiester bond linking the new residue to the terminus of the primer. The new 3'-hydroxyl group subsequently functions as a nucleophile towards the next incoming triphosphate. Selection of the dNTP derivative is dependent largely upon the rules of complementary affinity (e.g., G selects C, C selects G, A selects T and T selects A). Most chain terminating nucleosides function via elimination of the 3-hydroxyl substituent of the incoming dNTP after its incorporation. It has been discovered that absence of the 3'-hydroxyl in the furanosyl ring in the compounds of the invention effects chain termination in reverse transcriptase mediated polymerization, but not in syntheses mediated by human DNA polymerases. The ability of such nucleoside and nucleotide analog compounds to present themselves as substrates selectively to reverse transcriptase, in particular to HIV reverse transcriptase, coupled with their ability to effect chain termination, enables them to function as effective chain terminators specifically towards processes initiated by HIV reverse transcriptase without affecting the chain elongation process that is initiated by human DNA polymerases.

Examples of compounds of the present invention include triphosphate sugar derivatives of pyridine and pyrimidine bases, including deoxycytosine, deoxy and dideoxy thymine, deoxy and dideoxy uracil and related compounds. In one embodiment, the compounds of the invention comprise analogs of purine bases, including adenine and guanine analogs. The general classes of pyridine and pyrimidine analog compounds in a preferred embodiment of the invention are described by Formulas IIa–d. In another preferred embodiment, the nucleoside analogs are purine analog compounds of the invention are described by Formulas IIIa–d.

IIa
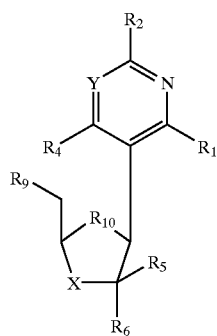

IIb
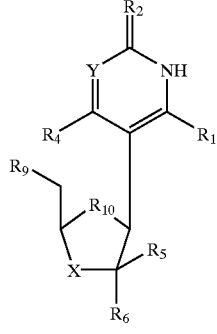

-continued

IIc
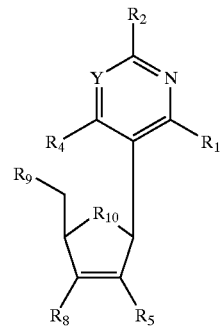

IId
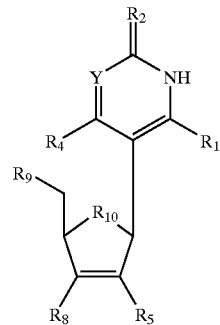

IIIa
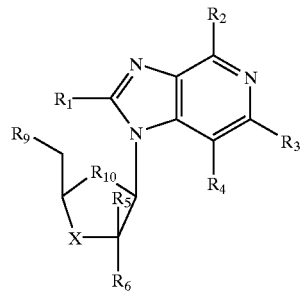

IIIb
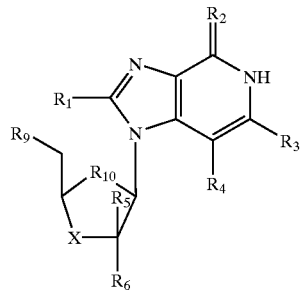

IIIc
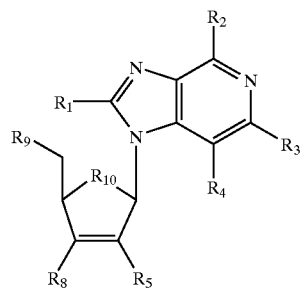

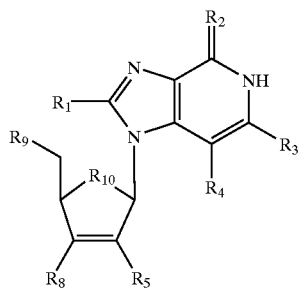

Figure 2:
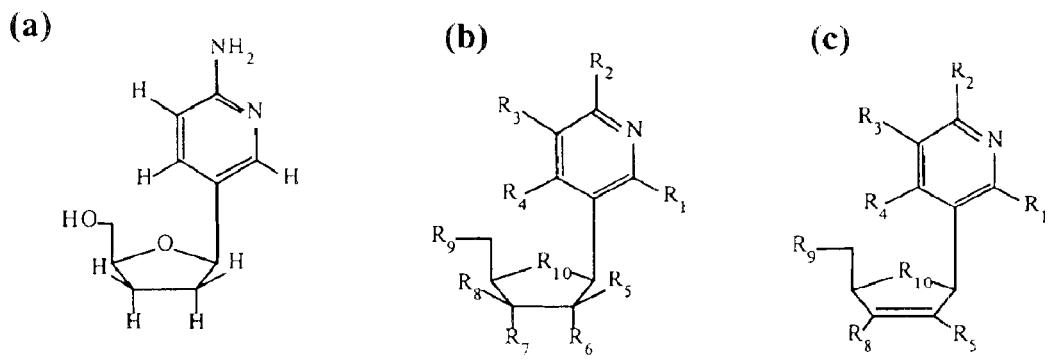
FIGS. 2–11 illustrate chemical structures of the compounds of the invention. Schemes pertaining to the synthesis of particular compositions are referenced in the Examples set forth herein.
Figure 3:
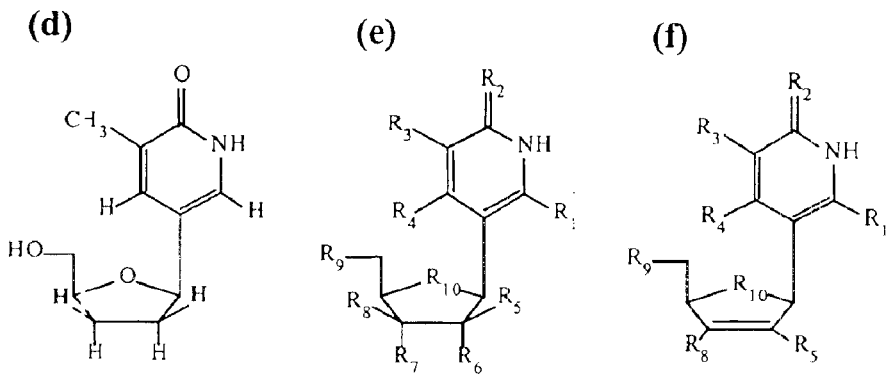
Figure 4:
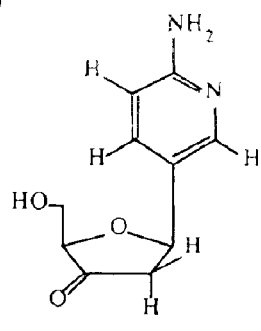
Figure 4:
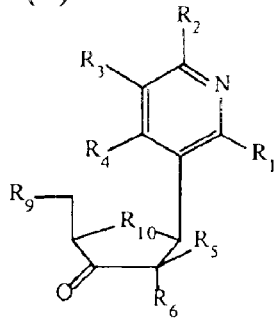
Figure 5:
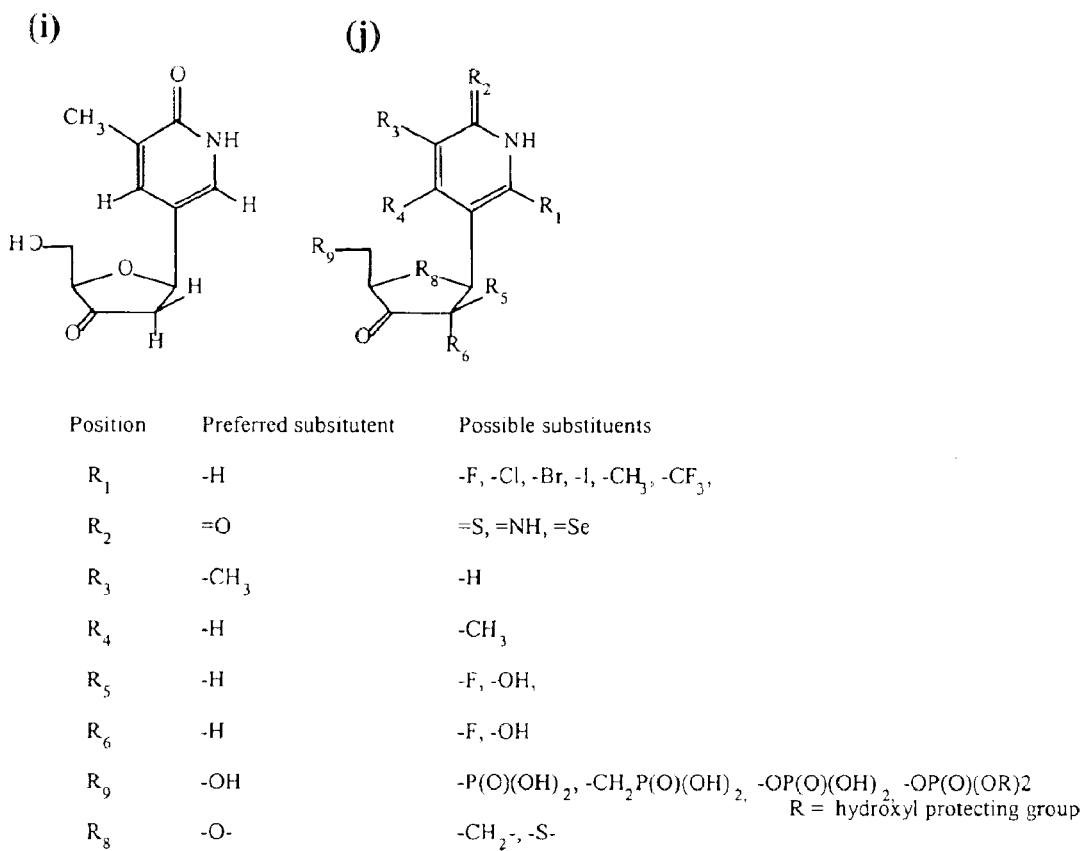
Figure 6:
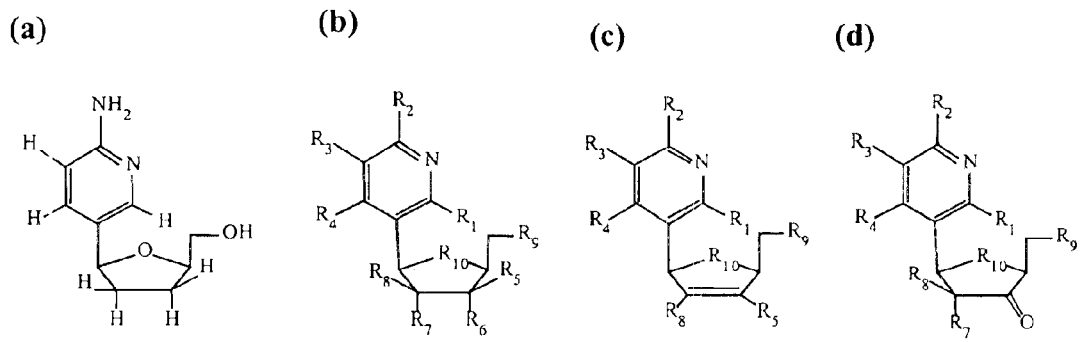
Figure 7:
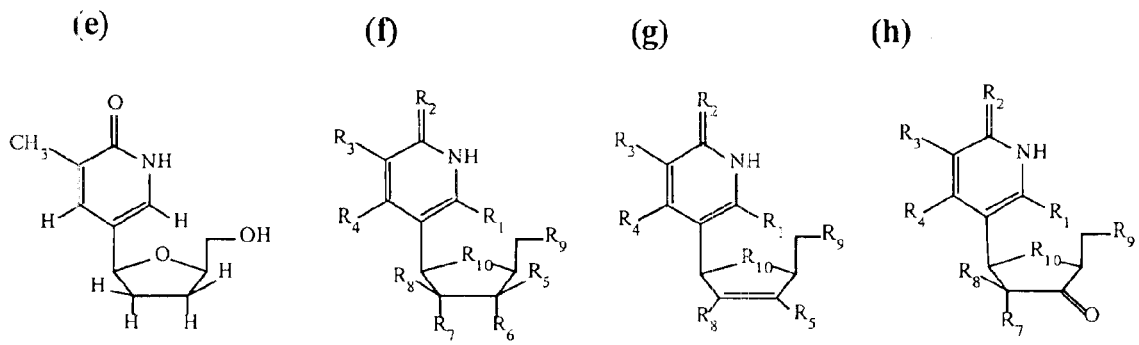
Figure 8:
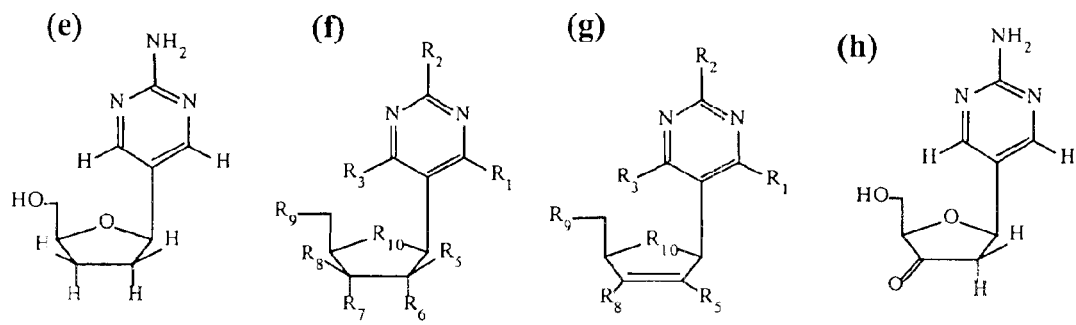
Figure 9:
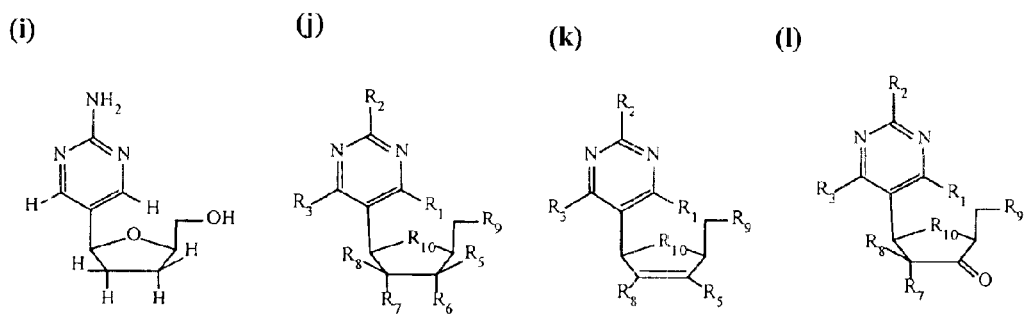
Figure 10:
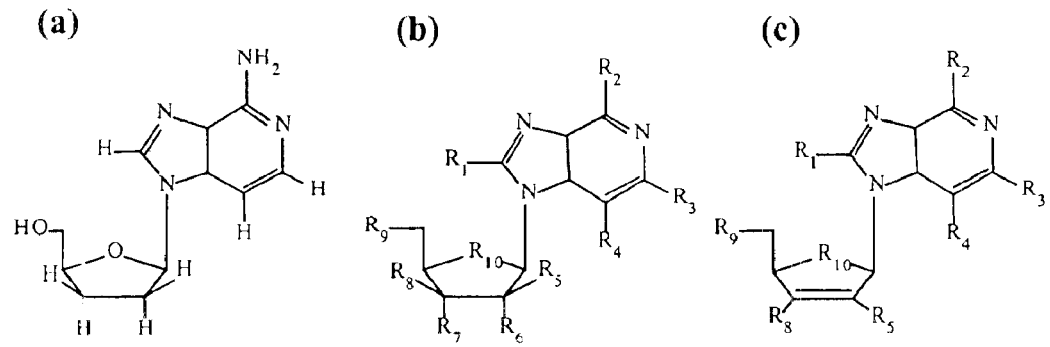
Figure 11:
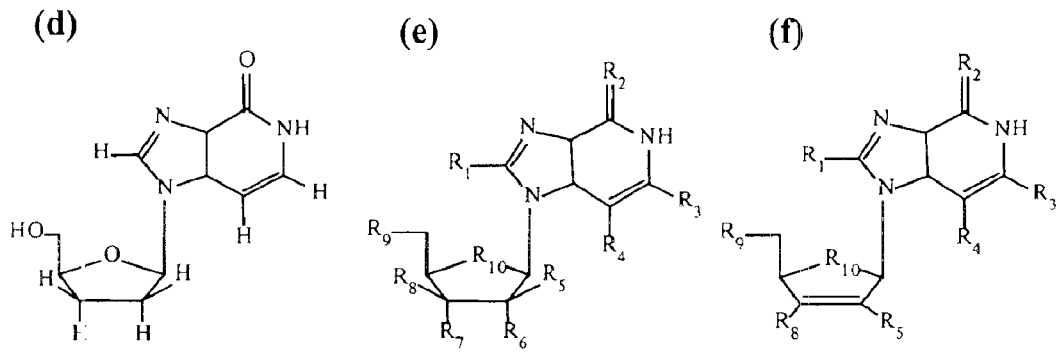

IIId wherein:
X=CO, CS, CR$_7$R$_8$
Y=CH,N
R$_1$ is H, F, Cl, Br, I, CH$_3$, CF$_3$
R$_2$ is NHR wherein R is lower alkyl comprising 1 to 6 carbons
R$_3$H, lower alkyl comprising 1 to 6 carbons, CH$_2$C≡CH, F, Cl, Br, I.
R$_4$=H, lower alkyl comprising 1 to 6 carbons, CH$_2$C≡CH
R$_5$=H, F, OH
R$_7$,=H, F, OH, N$_3^+$
R$_8$=H,F, OH
R$_9$=OH, P(O)(OH)$_2$, CH$_2$ P(O)(OH)$_2$, OP(O)(OH)$_2$, OP(O)(OR)$_2$ wherein R is a hydroxyl protecting group.
R$_{10}$=CH$_2$, O, S Compounds of the invention may be optical isomers that have D and L conformers. All single optical isomers, enantiomerically enriched isomers and combinations thereof, including racemic mixtures are included herein. Examples of D-pyridine analog compounds of the invention are shown in FIGS. 2(a–c) 3(d–f), (g,h) and 5(i,j); the corresponding L conformers are shown in FIGS. 6(a–d), 7(e–h). Examples of D-pyrimidine analog compounds of the invention are shown in FIG. 8(a–d); the corresponding L isomers are shown in FIG. 9(a–d). The general classes of D-purine analog compounds of the present invention are shown in FIGS. 10(a–c) and FIGS. 11(d–f); the corresponding L-isomers of the purine compounds are obtained in a manner analogous to the pyridine and purine compounds.

In a preferred embodiment, compounds of the present invention comprise 5'-triphosphate β-D-ribofuranosyl derivatives of pyridine and azabenzimidazole compounds, wherein the 3'-hydroxyl substituent in the furanose ring that is pre-requisite for subsequent elongation of the residue by the HIV reverse transcriptase is absent. In another preferred embodiment, 5'-triphosphate β-D-ribofuranosyl pyridine and its derivatives (wherein the 2' and 3'-hydroxy groups in the ribofuranosyl ring are eliminated) are obtained by reacting the corresponding (2',3'-dideoxy-β-D-ribofuranosyl)-pyridine compounds with trimethylphosphate, phosphorous oxychloride and tetra-n-butylammonium pyrophosphate (Scheme 1) to give the corresponding (2',3'-dideoxy-β-D-ribofuranosyl)-pyridine triphosphate compounds including 3-(2',3'-dideoxy-β-D-ribofuranosyl)-6-Amino-pyridine triphosphate (dd2ApyTP) as its tetra-n-butylammonium salt.

The nucleosides of the present invention wherein the critical 3'-hydroxy functional group is absent can still base pair effectively with their complementary partner and function as substrates for HIV reverse transcriptase, but substantially inert toward human polymerases. This type of enzyme discrimination on the basis of the heterocyclic moiety enables the development of potentially potent HIV chain terminators that are relatively less toxic to humans in comparison with presently known inhibitors.

Scheme 1

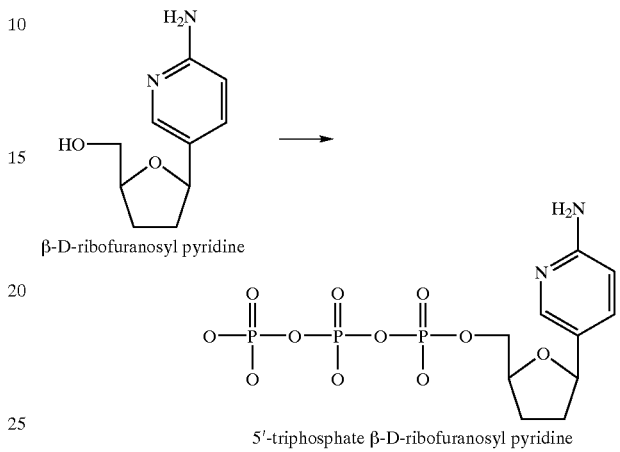

β-D-ribofuranosyl pyridine

5'-triphosphate β-D-ribofuranosyl pyridine

Compounds of the present invention include, but are not limited to, derivatives of pyrimidine and azabenzimidazole nucleoside analog derivatives, examples of which are shown below:

Pyridine derivatives

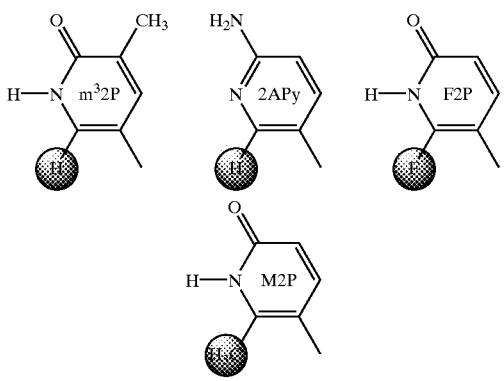

Azabenzimidazole derivatives

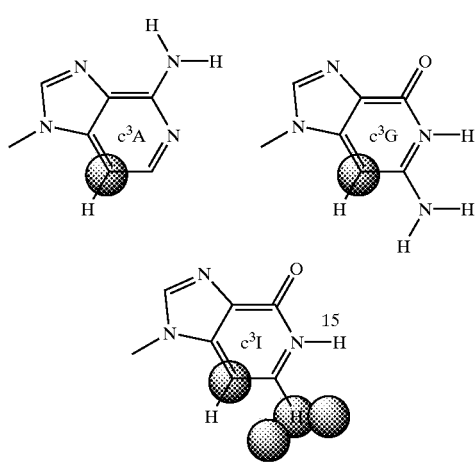

A synthetic scheme for 2-amino-5-(2',3'-dideoxyl-β-D-ribofuranosyl)-pyridine is shown and described in Scheme 2 below, which can be used to prepare the D-conformer of the 2APy type nucleosides and nucleotide analog derivatives of the invention.

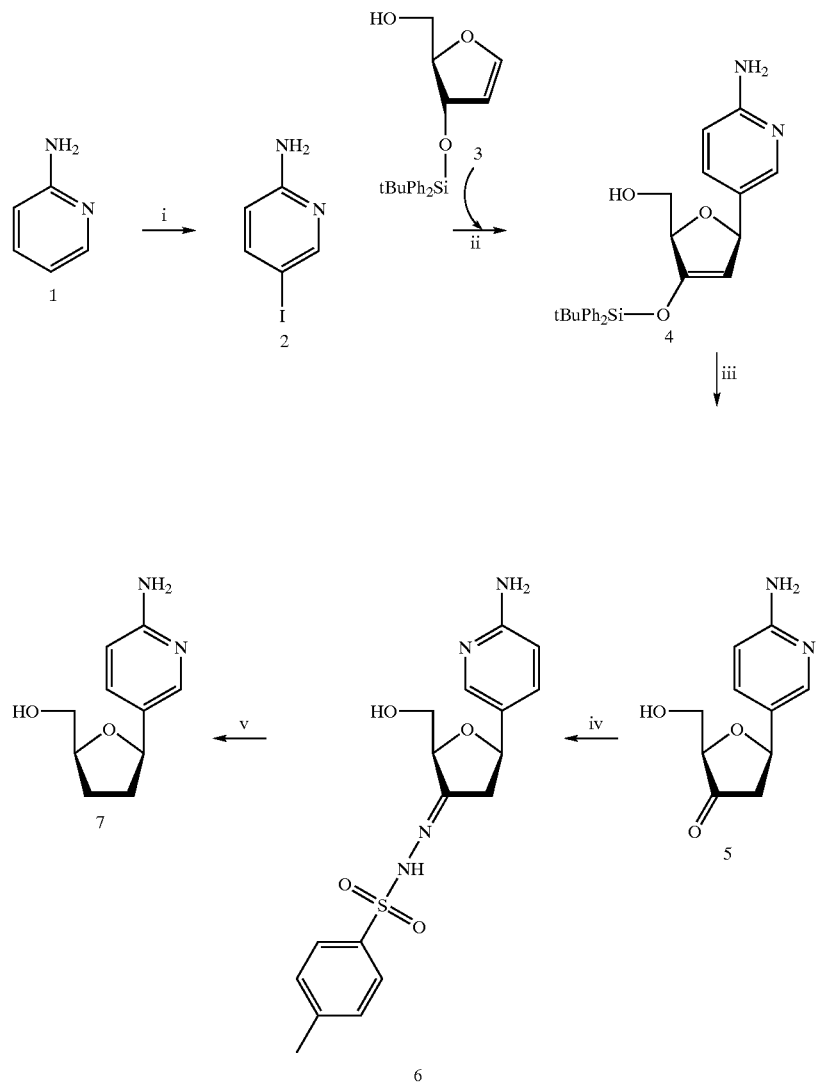

i. I$_2$/HIO$_4$/H$_2$SO$_4$/HOAc/H$_2$O, 80° C., 4h, 83%; ii. (dba)$_2$Pd$^0$/Ph$_3$P/iPr$_2$EtN/CH$_3$CN, 95° C., 30h, 92%; iii. nBu$_4$N$^+$F$^-$/CH$_3$COOH/THF, 0° C., 97%; iv. CH$_3$C$_6$H$_4$SO$_2$NHNH$_2$/MeOH, rt, overnight, 97%; v. NaHB(OAc)$_3$/HAc/CH$_3$CN, rt, 2h, 86%.

A synthetic scheme for 2-amino-5-(2',3'-dideoxyl-β-L-ribofuranosyl)-pyridine is shown and described in Scheme 3 below, which can be used to prepare the L-conformer of the 2APy type nucleosides and nucleotide analog derivatives of the invention.

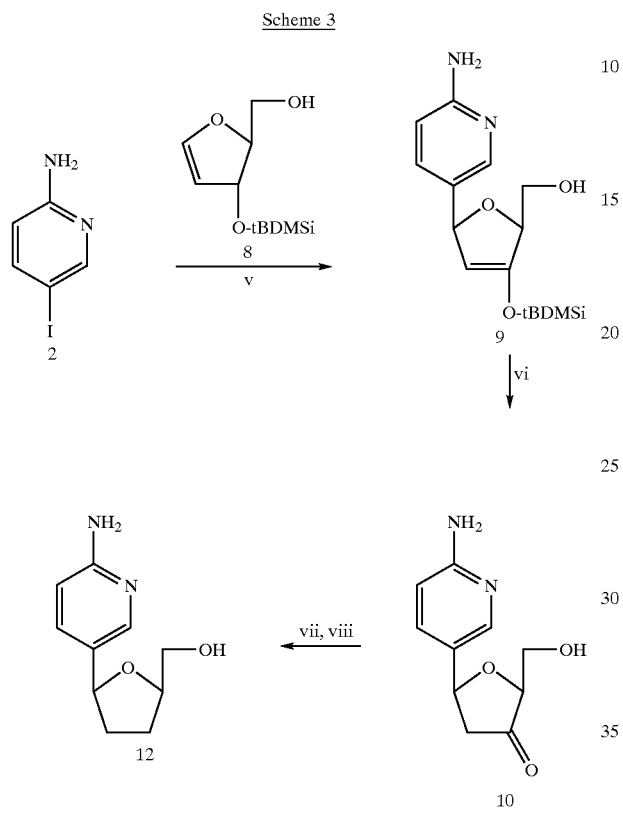

(vi) (dba)$_2$Pd$^O$/Ph$_3$P/i-Pr$_2$EtN/CH$_3$CN (vi) nBu$_4$N$^+$F (vii) p-toluylsulfonylhydrazide (viii) Na(OCOCH$_3$)$_3$BH, CH$_3$COOH/CH$_3$CN.

The compounds of the invention can be also obtained as the corresponding phosphate or phosphate derivative analogs. For example, the compounds of the invention can be a neutral 5'-phosphate derivative represented by compound IV shown below.

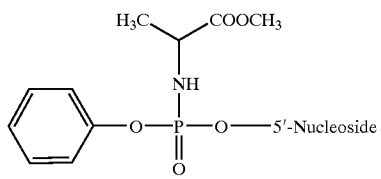

IV

In a one embodiment, the compound IV is a phosphoralaninate derivative of 2-amino-5-(2',3'-dideoxy-β-D-ribofuranosyl)-pyridine 13 (shown below), which is obtained by reacting 2-amino-5-(2',3'-dideoxy-β-D-ribofuranosyl)-pyridine 7 with a phosphoralaninate compound, such as for example, those described in the art (Qiu et al., *Antiviral Research*, (1999), 43(1), 37–53).

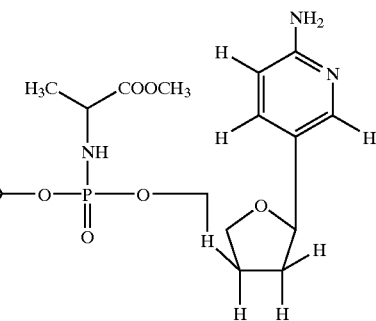

13

The nucleosides of the present invention wherein both the O2 carbonyl in the pyridine, pyrimidine and azabenzimidazole ring and the critical 3'-hydroxy functional group in the ribofuranosyl ring are both absent, can also be prepared according to the synthetic process shown in Scheme 4 below. The process results in the conversion of 2'-deoxynucleoside 14 to the corresponding 2',3'-dideoxynucleoside 17. In this procedure, the 5'-hydroxyl in 14 is protected in a high yield step with tBDMSi-Cl to give silyl ether 15. The 3'-OH is subsequently oxidized to the corresponding keto group in nearly quantitative yield using 1,1,1-triacetoxy-1,1-dihydro-1,2-benziodoxol-3-(1H)-one (Dess-Martin periodinane reagent). With a simple work up, without further purification, the 3'-keto derivative is converted to the corresponding hydrazone 16. The hydrazone is then reduced in high yield to the 2'3'-dideoxy compound 17.

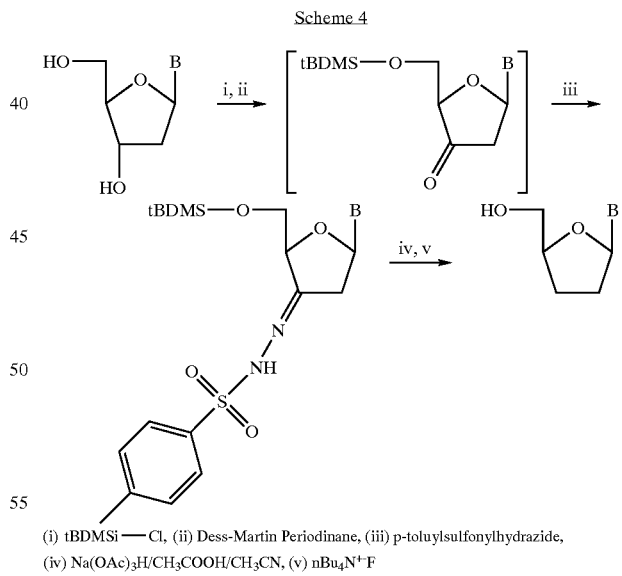

(i) tBDMSi—Cl, (ii) Dess-Martin Periodinane, (iii) p-toluylsulfonylhydrazide, (iv) Na(OAc)$_3$H/CH$_3$COOH/CH$_3$CN, (v) nBu$_4$N$^+$F Another method of affecting a similar transformation by the process of the invention utilizes a synthetic reaction sequence known in the art for deoxygenation of alcohols. (Robins, et al. *J. Am. Chem. Soc.* 1981, 103, 932, Id., Pankiewicz, K. et al., *J. Org. Chem.* 1982, 47, 485. Serafinowski, P. *Synthesis-Stuttgart,* 1990, 757). The 5'-OH of diol 14 is protected as a silyl ether, following which the 3'-OH is converted to thiocarbonate 18. Thiocarbonate 18 is then treated with Bu₃SnH and a free radical initiator such as AIBN to effect deoxygenation and yield the 2'3'-dideoxy compound 17 (Scheme 5).

Scheme 5

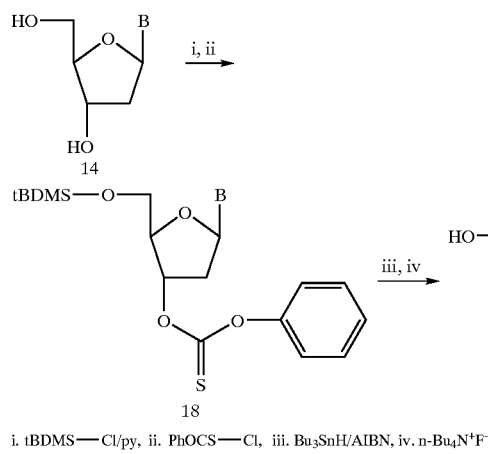

i. tBDMS—Cl/py, ii. PhOCS—Cl, iii. Bu₃SnH/AIBN, iv. n-Bu₄N⁺F⁻

A variation of the oxidation/reduction process described in Scheme 5 can also be used to convert ribonucleosides to 2'-deoxyribonucleosides by a method of the invention illustrated below in Scheme 6. The process involves protection of the 3'- and 5'-hydroxyls of triol 19 as the bis-silyl ether 20. The unprotected 2'-OH is then oxidized, converted to the corresponding hydrazone and reduced, following which removal of the bis-silyl ether group generates the 2'-deoxynucleoside 14.

Scheme 6

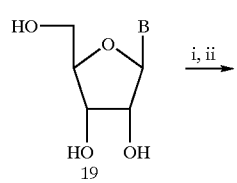

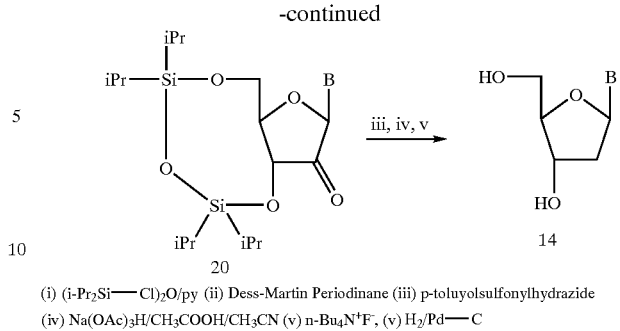

(i) (i-Pr₂Si—Cl)₂O/py (ii) Dess-Martin Periodinane (iii) p-toluyolsulfonylhydrazide
(iv) Na(OAc)₃H/CH₃COOH/CH₃CN (v) n-Bu₄N⁺F⁻, (v) H₂/Pd—C The present invention also provides an alternative deoxygenation method for the conversion of ribonucleosides to 2',3'-dideoxynucleosides as shown in Scheme 7 utilizing either methods a or b, wherein triol 19 is converted to alkene 20, followed by reduction to give 17.

Scheme 7

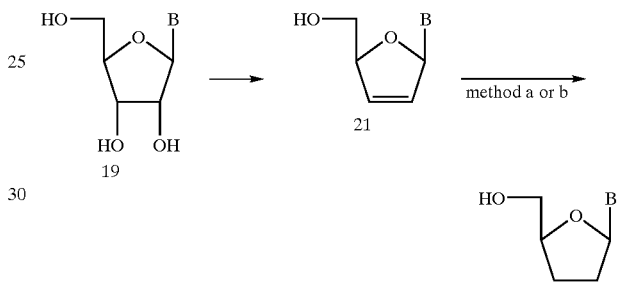

method a: (i) tBDMS—Cl, (ii) SOCl₂, (iii). NaIO₄·RuCl₃,
(iv). Na⁺naphthlenide, (v) n-Bu₄N⁺F⁻, (vi) H₂/Pd—C
method b: (i) tBDMS—Cl, (ii) Ms—Cl/py, (iii) Na₂Te, (iv) n-Bu₄N⁺F⁻,
(v) H₂/Pd—C.

Differential Selectivity Exhibited by Human DNA Polymerases and HIV Reverse Transcriptase Towards 2APy Type Analog Compound:

The differential selectivity between human DNA polymerases and HIV reverse transcriptase for compounds of the present invention as a substrate is illustrated in the experiment for the following primer/template complex:

| | | |
|---|---|---|
| 5' CAATAGGAACCCATGTACCGTAA (SEQ ID NO. 1) | ppp*C | 5'CAATAGGAACCCATGTACCGTAA*C (SEQ ID NO. 2) |
| 3' GTTATCCTTGGGTACATGGCATTGTCACTC (SEQ ID NO. 3) | → | 3' GTTATCCTTGGGTACATGGCATTGTCACTC (SEQ ID NO.3) | wherein ppp*C = dd2ApyTP =

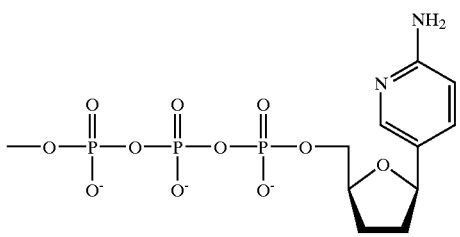

Figure 12:
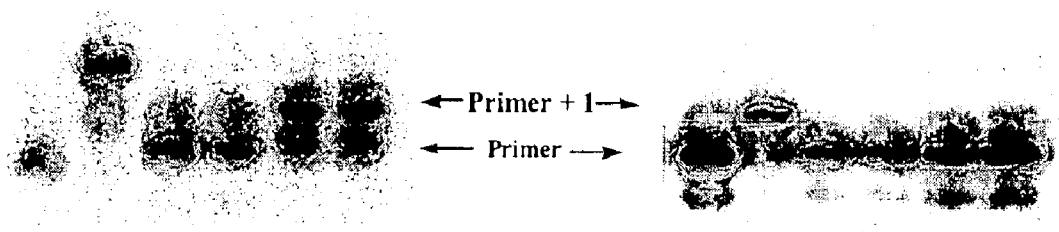
FIG. 12 is a gel chromatograph showing primer extensions exhibited by the nucleoside analogs using human polymerase β and HIV reverse transcriptase.
Figure 13:
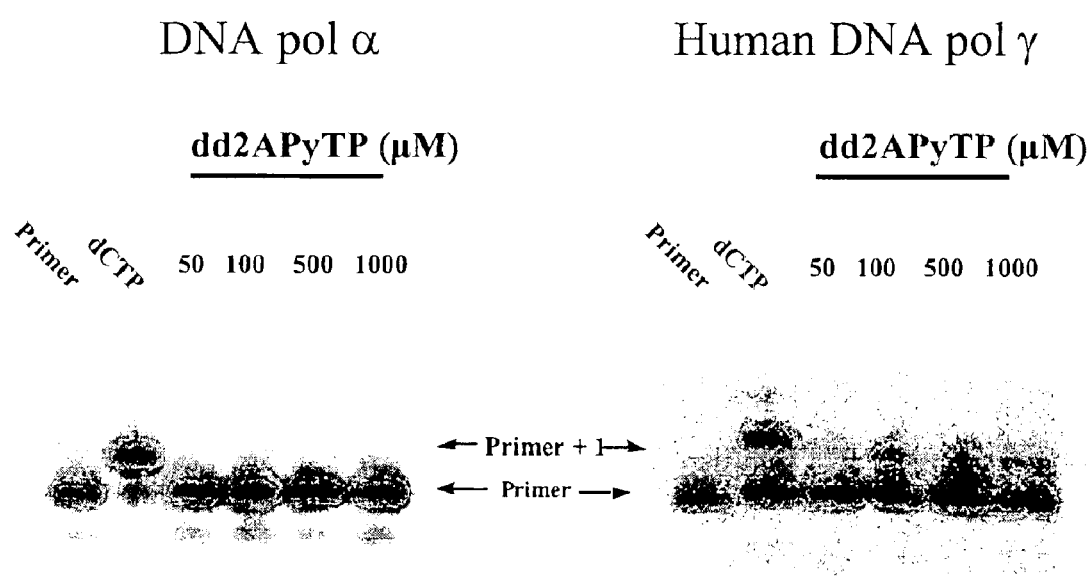
FIG. 13 is a gel chromatograph showing primer extensions exhibited by the nucleoside dd2ApyTP using human polymerase α and γ.

The nucleoside incorporation experiment for one of the modified nucleotide analog compounds of the present invention is illustrated in FIGS. 12 and 13. In FIG. 12, the right-hand side shows the results for human polymerase β and the left-hand side shows the results for HIV reverse transcriptase. The first nucleoside added to the primer should be a C residue (coded by the G residue of the template). A single triphosphate of dC or the above analog is offered to the enzyme/primer/template complex. The dCTP is incorporated by human polymerase β in the normal fashion and produces a band that is higher in the gel since the primer has been extended by one residue (dCTP lane, right-hand sides of FIG. 12). By comparison, this same experiment with the HIV RT results in two additions of the nucleoside, one specifically for a template dG residue and one nonspecifically. In the remaining lanes of the gel, experiments have been designed with only the analog dd2ApyTP present with the primer template complex. No incorporation is observed by the human polymerase β even after extensive incubation periods at any concentration of analog triphosphate. HIV reverse transcriptase is a less specific enzyme than DNA polymerase, and therefore exhibits different characteristics under identical conditions. As shown in FIG. 12 left, the n=1 elongation product is present at every concentration and the higher the concentration of analog triphosphate, the better is the incorporation.

FIG. 13 illustrates the results for polymerases α and γ. The dCTP experiment contains only the native dCTP triphosphate and normal incorporation into the primer in response to a template dG is observed for both enzymes. DNA polymerase α is unable to incorporate the analog dd2ApyTP regardless of concentration (left-side panel, FIG. 13). The results for DNA polymerase y are similar, although as the concentration of the analog triphosphate dd2ApyTP is increased, some minor amounts of incorporation are observed (right-hand panel, FIG. 13).

Compounds of the present invention can be used in the treatment of viral infections, especially retroviral infection such as those caused by HIV. Compounds of the present invention also may have therapeutic applications for treating HIV infections because they are specifically recognized and incorporated by HIV reverse transcriptase, but not by human DNA polymerases. The selectivity exhibited by compounds of the present invention provides a new class of potent inhibitors of HIV and other retroviruses with reduced mammalian toxicity, particularly in humans.

The modified nucleoside compounds of the present invention may be useful therapeutically as anti-viral drugs. They may also be incorporated into RNA, which may be useful for diagnostic applications. The nucleoside compounds of the invention can also be used, either alone or in combination with, other modified nucleosides and/or naturally occurring nucleosides, to prepare oligonucleotides. The general principles for their use in said applications are summarized below.

Use as Antiviral Compounds

Several modified nucleosides are known to possess antiviral activity. These are often modified nucleosides, where the modification is at the 2' or 3' positions. Modified nucleosides can inhibit viral replication by inhibiting viral thymidine kinase by slowing replication. Replication is slowed by reducing the amount of nucleotide monophosphates available. Alternatively, nucleoside analogs like acyclovir take advantage of the different specificity of the thymidine kinases, viral and human, by only being phosphorylated by the viral enzyme. The phosphorylated nucleoside is subsequently incorporated by the infected cells, resulting in chain termination and cell death. The nucleoside compounds of the invention can be modified in a manner so as to be phosphorylated by viral kinases, in preference to the human kinases, leading to specificity and reduced toxicity. Modifications that result in increased specificity to viral kinases are well known to those of skill in the art. For example, the 3' position can be modified to contain an azide moiety, as in AZT. The structural modifications at the 2' and 3' positions of the ribofuranosyl ring, the modified nucleoside analog compounds of the invention are therefore, capable of have anti-viral activity similar to AZT. In addition, the compounds of the invention, unlike AZT, due to the absence of the O2 carbonyl in the nucleobase segment of the molecules are expected to be chemically inert to the host cell. Compounds of the invention are therefore capable of exhibiting selective antiviral activity while maintaining substantially reduced toxicity. Methods for screening anti-viral activity are well known to those of skill in the art. Methods for administering nucleic acid-based protease inhibitors, such as AZT and ddI, to humans for tratedment of viral diseases such as HIV also are known.

Pre- and Post-SELEX Modification

The nucleoside compounds of the invention can be used to prepare oligonucleotides, either alone or in combination with other modified nucleosides and/or naturally occurring nucleosides. One problem associated with using naturally occurring nucleosides in therapeutic and in vivo diagnostic uses is that the oligonucleotides in their phosphodiester form may be quickly degraded in body fluids by intracellular and extracellular enzymes such as endonucleases and exonucleases before the desired effect is manifest. Chemically modified nucleosides have been known to increase the in vivo stability of the oligonucleotides. It is preferred that the nucleosides be modified in such a way as to provide increased in vivo stability. When the nucleosides are used to prepare oligonucleotides according to the Systematic Evolution of Ligands by Exponential Enrichment (SELEX) methodology, they can be used in both pre- and post-SELEX modification. Pre-SELEX modifications yield oligonucleotides with both specificity for their SELEX target and improved in vivo stability. Post-SELEX modifications made to nucleosides can result in improved in vivo stability without adversely affecting the binding or interacting capacity of the oligonucleotides.

Diagnostic Uses

Nucleosides of the invention when modified to contain a radiolabel, a fluorescent tag such as rhodamine or fluorescein, are biotinylated, can be detected after the nucleoside is incorporated into viral RNA. Such embodiments are particularly useful as in vivo or in vitro diagnostics, e.g. for detection of HIV. Oligonucleotides that include the modified nucleosides of the invention can also be labeled, and when they specifically bind to or interact with a target site, the binding or interaction can be observed by detecting the label. This can be useful as a diagnostic tool, to determine whether a particular binding site is present in a sample by adding a specific oligonucleotide that selectively binds to or interacts with the site, washing away unbound oligonucleotide, and observing binding or interaction by looking for the label.

The synthesis of examples of the compounds of the invention and their ability to selectively react with viral reverse transcriptase is described in the following examples, which are not intended to be limiting in any manner with regards to the scope of the invention.

EXAMPLES

I. Synthesis of 2-amino-5-(2',3'-dideoxy-β-D-ribofuranosyl)-pyridine

In general, compounds of the present invention are synthesized according to the synthetic methods described below. The methods utilized to synthesize the present compounds represents modifications of literature procedures. The references from which related chemical reactions have been modified to provide the present compounds are set forth in the examples below. Spectroscopic and spectrophotometric analyses for chemical characterization of the present compounds were conducted using standard analytical methods.

Example 1
2-Amino-5-iodopyridine (2)

The iodo compound 2 was prepared by a standard method. A mixture of 2-aminopyridine (1) (2.4 g, 25 mmol), periodic acid dihydrate (0.86 g, 3.75 mmol), and iodine (2.7 g, 10.7 mmol) were heated in a mixed solution of acetic acid (60 ml), water (3 ml), and sulfuric acid (0.5 ml) at 80° C. for 4 h. It was then poured into 10% aqueous $Na_2S_2O_3$ solution to remove unreacted iodine and extracted with ether. The extract was washed with 10% aqueous NaOH, dried ($K_2CO_3$), and concentrated in vacuo. The residue was purified by flash chromatography on silica gel (eluted with ethyl acetate/hexanes 5:2; $R_f$=0.64), followed by recrystallization from ethanol to give colorless prisms of compound 2 (83% yield, 4.6 g). UV-vis: max ($CH_3OH$) 247 (46330), 314 nm (7970); IR (KBr): 3377(s), 3301(s), 3144(sb), 3012(m), 1640(s), 1577(s), 1545(s), 1483(s), 1381(s), 1312(s), 1256 (s), 1142(s), 1086(s), 998(s), 828(s), 526(s), 457(s)cm −1; $^1$H NMR (400 MHz, $CDCl_3$, ppm): 8.21(s,1H), 7.62(d, J=8 Hz, 1H), 6.35 (d, J=8 Hz, 1H), 4.51(s, 2H); 13C NMR (100 MHz, $CDCl_3$, ppm): 157.30, 153.73, 145.31, 110.96, 78.00. MP: 128–129° C. HRMS: calculated (m/e) for $C_5H_4IN_2$(M+1): 220.9576; found, 220.9576.

Example 2
5-(-D-glyceropentofuran-3'-ulos-1'-yl)-2-amino-pyridine (5)

A mixture of bis(dibenzylideneacetone)palladium(0) (0.115 g, 0.2 mmol) and tris(pentafluorophenyl)phosphine (0.213 g, 0.4 mmol) in acetonitrile (60 ml) was stirred under nitrogen at room temperature for 30 min. Then, N,N-diisopropylethylamine (1.4 ml, 8 mmol), 1,4-anhydro-2-deoxy-3-O-(1,1-dimethylethyl)diphenylsilyl-D-erythro-1-enitol (3) (1.42 g, 4 mmol) and 2 (0.880 g, 4 mmol) were added in above mixture. The resulting reaction solution was refluxed under nitrogen at 95° C. for 30 h. The volatiles were removed in vacuo. The residue was purified by flash chromatography on silica gel (eluent: methylene chloride/methanol =9:1, $R_f$=0.37) to yield intermediate 4 (1.7 g, 92% yield) as colorless foam slightly contaminated by trace amount of N,N-diisopropylethylamine. The characteristics of 4 is as follows: $^1$H NMR (400 MHz, $CDCl_3$, ppm): 7.86–7.83(m, 2H), 7.77–7.72(m, 3H), 7.47–7.741(m, 6H), 7.07(dd, 1H, J=2.4 Hz), 6.27(d, 1H, J=8.4 Hz), 5.43(d, 1H, J=2.8 Hz), 4.67–4.65(m, 1H), 4.22–4.20(m, 1H), 3.85–3.80 (m, 2H), 1.09(s, 9H).

To a solution of compound 4 (1.7 g, 3.7 mmol) in THF (20 ml) at 0° C. was added acetic acid (0.88 ml, 16 mmol) followed by 8 ml of an 1 M solution of tetra-n-butyl-ammonium fluoride in THF (8 mmol). The desilylation reaction was completed in 40 min. based on TLC analysis. The volatiles were removed, and the residue was separated by flash chromatography (eluted with $CH_2Cl_2/CH_3OH$=9:1, $R_f$=0.23) to afford compound 5 (0.74 g). Yield for two steps was 89%. UV-vis: max ($CH_3OH$) 239 (15570), 300 (3910) nm; IR(KBr): 3440(s), 3325(sb), 3204(sb), 3053(w), 2950 (w), 2921(w), 28819w), 2857(w), 28239w), 1761(s), 1634 (s), 1611(s), 15139s), 14219s0, 1323(s), 1161(s), 1103(s), 844(s), 775(m)cm–1; $^1$H NMR (400 MHz, CD3OD, ppm): 7.97 (d, 1H, J=2.4 Hz), 7.68 (dd, 1H, J1=2.4, J2=8.8 Hz), 6.61(d, 1H, J=8.8 Hz), 5.08 (dd, 1H, J1=6.0, J2=11.2 Hz), 3.98 (t, 1H, J=3.2 Hz), 3.82 (d, 2H, 3.2 Hz), 2.75 (dd, 1H, J1=6.0 Hz, J2=17.2 Hz), 2.45 (dd, 1H, J1=11.2 Hz, J2=17.2 Hz); $^{13}$C NMR (100 MHz, $CD_3OD$, ppm): 215.56, 160.99, 146.67, 138.19, 126.09, 110.44, 84.38, 76.89, 62.04, 46.19. MP: 140° C. decompose; HRMS: calculated for $C_{10}H_{13}N_2O_3$(M+1): 209.0926; found: 209.0926.

Example 3
5-((-)-D-glyceropentofuran-3'-ulos-1'-yl)-2-aminopyridine p-toluenesulfonyl-hydrazone (6)

To 1 g(4.8 mmoles) of compound 5 in 30 ml of methanol was added 1.8 g(9.6 mmoles) of p-toluenesulfonylhydrazide. The solution was stirred at room temperature for overnight. Crystallization from methanol gave hydrazone compound 5 (1.75 g, yield 97%). UV-vis: max ($CH_3OH$) 273, 300 nm; IR(KBr): 3741(s), 3370(s), 3213(s), 3026(m), 2923(m), 2845(m), 1677(s), 1639(s), 1515(m), 1337(s), 1167(s), 1041(s), 941(m), 551 (s)cm−1; $^1$H NMR (400 DMSO, ppm) 10.33(sb, 1H), 7.86 (d, 1H, J=1.6 Hz), 7.71(d, 2H, J=8 Hz), 7.40–7.38(m, 3H), 6.41(d, 1H, J=8.4 Hz), 5.96(s, 2H), 4.76–4.72(m, 2H), 4.20–4.19(m, 1H), 3.61–3.57(m, 1H), 3.39–3.31(m, 1H), 2.92(dd, 1H, J1=6 Hz, J2=17.6 Hz), 2.29(ddd, 1H, J1=2 Hz, J2=10 Hz, J3=17.6 Hz); 13C NMR (100 MHz, DMSO, ppm): 161.52, 159.53, 146.29, 143.03, 135.92, 135.51, 129.25, 127.18, 123.01, 107.58, 80.73, 76.55, 62.85, 36.93, 21.09; MP: 150° C. decomp.; HRMS: calculated for $C_{17}H_{21}N_4O_4S$(M+1): 377.1284; found: 377.1283.

Example 4
2-amino-5-(2',3'-dideoxyl-D-ribofuranosyl)-pyridine (7)

To 377 mg (1 mmole) of compound 6 in 20 ml of 1:1 mixture of acetic acid and acetonitrile 424 mg (2 mmoles) of sodium triacetoxyborohydride was added at 0° C. The mixture was stirred for 2 h. Volatiles were then removed in vacuo, and the resulting residue was purified by column chromatography on silica gel(eluted with methanol/methylene chloride, 1:9) to give compound 7(168 mg, 86%). UV-vis: max ($CH_3OH$) 273, 300 nm; IR (KBr): 3345(sb), 3225(m), 2923(m), 2867(m), 1627(s), 1501(s), 1420(m), 1356(m), 1041(s); $^1$H NMR (400 MHz, $CDCl_3$, ppm) 7.96

(s,1H), 7.41(d, 1H, J=8.4 Hz), 4.75–4.72(m,1H), 4.59(sb, 2H), 4.14–4.08(m,1H), 3.74(dd, 1H, J1=3.6 Hz, J2=11.6 Hz), 3.59(dd, 1H, J1=6 Hz, J2=12 Hz), 2.22–2.15(m,1H), 2.06–1.97(m,1H), 1.87–1.73(m,2H); $^{13}$C NMR (100 MHz, CD$_3$OD,ppm) 158.13, 146.13, 136.33, 127.17, 108.69, 80.19, 79.59, 65.22, 33.92, 27.88; HRMS: calculate for C$_{10}$H$_{14}$N$_2$O$_2$ (M): 194.1055; found: 194.1059.

Example 5
5-(-L-glyceropentofuran-3'-ulos-1'-yl)-2-amino-pyridine (10)

A mixture of bis-(dibenzylideneacetone)-palladium(0) (0.115 g, 0.2 mmol) and tris-(pentafluorophenyl)-phosphine (0.213 g, 0.4 mmol) in acetonitrile (60 ml) was stirred under nitrogen at room temperature for 30 min. Then, N,N-diisopropylethylamine (1.4 ml, 8 mmol), 1,4-anhydro-2-deoxy-3-O-(1,1-dimethylethyl)diphenylsilyl-L-erythro-1-enitol (8) (800 mg, 2.25 mmol) and 2 (500 mg, 2.27 mmol) were added in above mixture. The resulting reaction solution was refluxed under nitrogen at 95° C. for 30 h. The volatiles were removed in vacuo. The residue was purified by flash chromatography on silica gel (eluent: methylene chloride/methanol=9:1, R$_f$=0.37) to yield intermediate 9 (935 mg, 93% yield) as colorless foam. The characteristics of 9 is as follows: $^1$H NMR (400 MHz, CDCl$_3$, ppm): 7.86–7.83 (m, 2H), 7.77–7.72 (m, 3H), 7.47–7.741 (m, 6H), 7.07 (dd, 1H, J=2.4 Hz), 6.27 (d, 1H, J=8.4 Hz), 5.43 (d, 1H, J=2.8 Hz), 4.67–4.65 (m, 1H), 4.22–4.20 (m, 1H), 3.85–3.80 (m, 2H), 1.09(s, 9H).

To a solution of compound 9 (935 mg, 2.09 mmol) in THF (20 ml) at 0° C. was added acetic acid (0.5 ml), followed by 3 ml of an 1 M solution of tetra-n-butyl-ammonium fluoride in THF (3 mmol). The desilylation reaction was completed in 40 min. based on TLC analysis. The volatiles were removed, and the residue was separated by flash chromatography (eluted with CH$_2$Cl$_2$/CH$_3$OH=9:1, R$_f$=0.23) to afford compound 10 (426 mg). Yield for two steps was 91%. UV-vis: max (CH$_3$OH) 239 (15570), 300 (3910) nm; IR (KBr): 3440(s), 3325(sb), 3204(sb), 3053(w), 2950(w), 2921(w), 28819w), 2857(w), 28239w), 1761(s), 1634(s), 1611(s), 15139s), 14219s0, 1323(s), 1161(s), 1103(s), 844 (s), 775 (m)cm−1; $^1$H NMR (400 MHz, CD3OD, ppm): 7.97 (d, 1H, J=2.4 Hz), 7.68 (dd, 1H, J1=2.4, J2=8.8 Hz), 6.61 (d, 1H, J=8.8 Hz), 5.08 (dd, 1H, J1=6.0, J2=11.2 Hz), 3.98 (t, 1H, J=3.2 Hz), 3.82 (d, 2H, 3.2 Hz), 2.75 (dd, 1H, J1=6.0 Hz, J2=17.2 Hz), 2.45 (dd, 1H, J1=11.2 Hz, J2=17.2 Hz); $^{13}$C NMR (100 MHz, CD$_3$OD, ppm): 215.56, 160.99, 146.67, 138.19, 126.09, 110.44, 84.38, 76.89, 62.04, 46.19. MP: 140° C. decompose; HRMS: calculated for C$_{10}$H$_{13}$N$_2$O$_3$ (M+1): 209.0926; found: 209.0926.

Example 6
5-(-L-glyceropentofuran-3'-ulos-1'-yl)-2-aminopyridine p-toluenesulfonyl-hydrazone (11)

To 250 mg (1.2 mmoles) of compound 10 in 10 ml of methanol was added 437 mg (2.4 mmoles) of p-toluenesulfonylhydrazide. The solution was stirred at room temperature for overnight. Crystallization from methanol gave hydrazone compound 11 (443 mg, yield 98%). UV-vis: max (CH$_3$OH) 273, 300 nm; IR (KBr): 3741(s), 3370(s), 3213(s), 3026(m), 2923(m), 2845(m), 1677(s), 1639(s), 1515(m), 1337(s), 1167(s), 1041(s), 941(m), 551 (s)cm−1; $^1$H NMR (400 MHz, DMSO, ppm) 10.33(sb, 1H), 7.86 (d, 1H, J=1.6 Hz), 7.71 (d, 2H, J=8 Hz), 7.40–7.38 (m, 3H), 6.41 (d, 1H, J=8.4 Hz), 5.96 (s, 2H), 4.76–4.72 (m, 2H), 4.20–4.19 (m, 1H), 3.61–3.57 (m, 1H), 3.39–3.31 (m, 1H), 2.92 (dd, 1H, J1=6 Hz, J2=17.6 Hz), 2.29 (ddd, 1H, J1–2 Hz, J2=10 Hz, J3=17.6 Hz); $^{13}$C NMR (100 MHz, DMSO, ppm): 161.52, 159.53, 146.29, 143.03, 135.92, 135.51, 129.25, 127.18, 123.01, 107.58, 80.73, 76.55, 62.85, 36.93, 21.09; MP: 150° C. decompose; HRMS: calculated for C$_{17}$H$_{21}$N$_4$O$_4$S (M+1): 377.1284; found: 377.1284.

Example 7
2-amino-5-(2',3'-dideoxyl-β-L-ribofuranosyl)-pyridine (12)

To 200 mg (0.53 mmole) of compound 11 in 10 ml of 1:1 mixture of acetic acid and acetonitrile 318 mg (1.5 mmoles) of sodium triacetoxyborohydride was added at 0° C. The mixture was stirred for 1 h. Volatiles were then removed in vacuo, and the resulting residue was purified by column chromatography on silica gel (eluted with methanol/methylene chloride, 1:9) to give compound 12 (89 mg, 87%). UV-vis: max (CH$_3$OH) 273, 300 nm; IR (KBr): 3345(sb), 3225(m), 2923(m), 2867(m), 1627(s), 1501(s), 1420(m), 1356(m), 1041(s); $^1$H NMR (400 MHz, CDCl3, ppm) 7.96(s, 1H), 7.41 (d, 1H, J=8.4 Hz), 4.75–4.72 (m,1H), 4.59 (sb, 2H), 4.14–4.08 (m, 1H), 3.74 (dd, 1H, J1=3.6 Hz, J2=11.6 Hz), 3.59 (dd, 1H, J1=6 Hz, J2=12 Hz), 2.22–2.15 (m, 1H), 2.06–1.97 (m,1H), 1.87–1.73 (m, 2H); $^{13}$C NMR (100 MHz, CD$_3$OD, ppm) 158.13, 146.13, 136.33, 127.17, 108.69, 80.19, 79.59, 65.22, 33.92, 27.88; HRMS: calculated for C$_{10}$H$_{14}$N$_2$O$_2$ (M): 194.1055; found: 194.1056.

II. Biological Activity

Example 8
General Procedure for Chain Termination and Primer Extension

The following buffers were used for each polymerase: DNA polmerase α, 50 mM Tris.HCl pH 8.0, 5 mM Mg(AcO)$_2$, 1 mM DTT, 1 mM spermidine; DNA pol β 50 mM Tris.HCl pH 8.0, 10 mM MgCl$_2$, 1 mM DTT; DNA Polymerase γ 50 mM Tris.HCl pH 7.5, 100 mM NaCl, 2.5 MM MgCl$_2$; HIV RT 50 mM Tris.HCl pH 8.5, 10 mM MgCl$_2$, 40 mM KCl, 1 mM DTT. Template, primer and the corresponding buffer were mixed and heated to 100° C. for 1 min, allowed to cool to room temperature then placed on ice for 30 min. Once the template and primer had been allowed to anneal the polymerase was added. The appropriate amount of template-primer mixture was added to a vial containing water and the NTP(s) at the desired concentration. Typical reaction volumes were 10 μL. The reactions were incubated at 37° C. for 45 min. The reactions were quenched using Na-EDTA, heated at 100° C. for 1 min, and then flash frozen in liquid N$_2$. Primer extensions were analyzed by standard methods by denaturing Polyacrylamide Gel Electrophoresis (PAGE).

Example 9
Gel Electrophoresis

Analytical polyacrylamide gel electrophoresis was performed using a 38×50 cm Sequi-Gen GT sequencing cell with a thickness of 0.4 mm and 15% monomer (acrylamide:bisacrylamide 19:1). Gels were run using 90 mM Tris-Borate 1 mM EDTA buffer (pH 8.3). Gels were imaged on Phosphorimager: 425 from Molecular Dynamics (Sunnyvale, Calif.).

What is claimed is:

1. A compound of the formula:

wherein B = 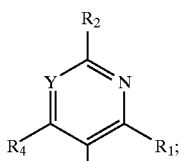    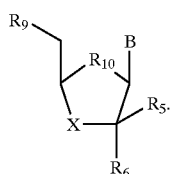

X represents $CR_7R_8$;

Y represents $CR_3$ or N;

$R_1$ represents H, F, Cl, Br, I, $CH_3$ or $CF_3$;

$R_2$ represents NHR wherein R is H, lower straight or branched chain alkyl alkenyl or alkynyl consisting of 1 to 6 carbons;

$R_3$ is H, lower straight or branched chain alkyl alkenyl or alkynyl consisting of 1 to 6 carbons, F, Cl, Br, or I;

$R_5$ is H, F or OH;

$R_6$ is H, F or OH;

with the proviso that when either of $R_5$ and $R_6$ is OH, then $R_6$ or $R_5$, respectively, cannot be either OH or F;

$R_7$ and $R_8$ independently represent H;

$R_9$ is OH or 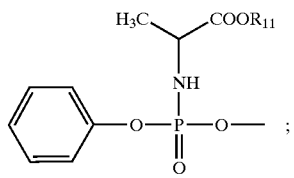 ;

wherein $R_{11}$ is straight or branched alkyl; and $R_{10}$ represents $CH_2$, O, or S, or a 5'-triphosphate derivative therof, phamaceutically acceptable complex or a pharmaceutically acceptable salt thereof.

2. A compound of claim 1 wherein

B = 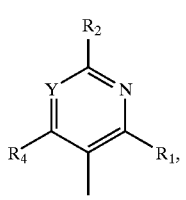    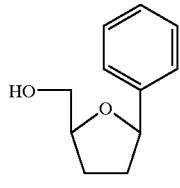

X is $CR_7R_8$;

Y is $CR_3$;

$R_1$, $R_3$, $R_4$, $R_5$, $R_6$, $R_7$ and $R_8$ are H;

$R_2$ is $NH_2$;

$R_9$ is OH, or 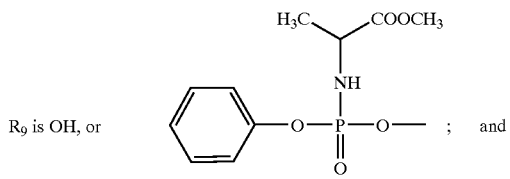 ; and $R_{10}$ is O, or a 5'-triphosphate derivative thereof, pharmaceutically acceptable complex or a pharmaceutically acceptable salt thereof.

3. A compound of claim 1 wherein the compound is the D isomer, the L isomer, mixtures thereof, or a racemate.

4. A compound of claim 1 which is 2-amino-5-(2',3'-dideoxy-β-D-ribofuranosyl)-pyridine, 2-amino-5-(2',3'-dideoxy-β-L-ribofuranosyl)-pyridine, mixtures thereof and racemic 2-amino-5-(2',3'-dideoxy-β-ribofuranosyl)-pyridine.

5. A method of selectively inhibiting HIV, in a host in need thereof by administration of an effective amount of a compound of claim 1.

6. A process for preparation of a compound of claim 1 comprising the steps of:

i) selectively protecting the 5'-hydroxyl group of a 2'-deoxyribonucleoside analog precursor;

iia) oxidation of the unprotected 3'-hydroxyl group into the corresponding 3'-ketone group;

iib) converting the 3'-ketone group to the corresponding 3'-hydrazone; OR iiia) converting the 3'-hydroxyl group of the product of step i) to a thiocarbonate group; OR iva) converting the 2'- and 3'-hydroxyl groups of the product of step i) into a 2',3'-cyclic silyl ether;

v) reduction of the product of step iib), step iiia) or step iva) to produce a 3'-methylene group; and vi) the 5'-protecting group is removed by hydrolysis.

7. A pharmaceutical composition which comprises as active ingredient a compound according to claim 1 or a pharmaceutically acceptable salt, ester, or the 5'-mono, di- or tri phosphate thereof, in combination with a pharmaceutically acceptable carrier.

8. The composition of claim 7 wherein the carrier is suitable for intravenous delivery, parenteral delivery or oral administration.

9. A process for preparation of a compound of claim 1 comprising the steps of:

i) selectively protecting the 5'-hydroxyl group of a 2'-deoxyribonucleoside analog precursor;

ii) converting the 3'-OH to a thiocarbonate;

iii) treating the thiocarbonate with $Bu_3SnH$ and a free radical initiator to effect deoxygenation; and iv) the 5'-protecting group is removed by hydrolysis.

10. A compound of formula:

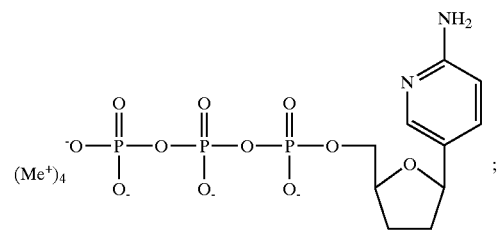

wherein the term $Me^+$ is defined to be a pharmaceutically acceptable monocation.

11. A compound of the formula:

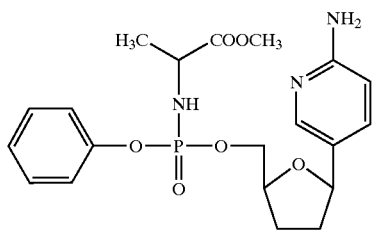

12. A compound of the formula:

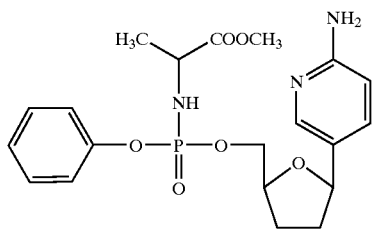

13. A compound of formula:

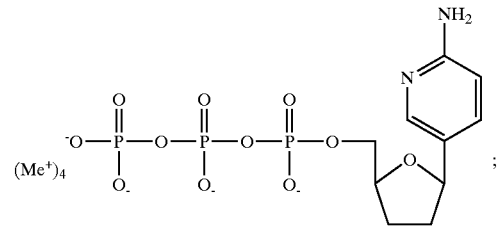

wherein the term $Me^+$ is defined to be a pharmaceutically acceptable monocation.

14. The method of claim 5 wherein the compound is represented by the formula:

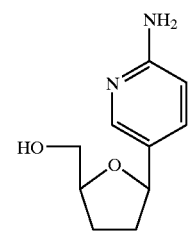

15. The method of claim 5 wherein the compound is represented by the formula:

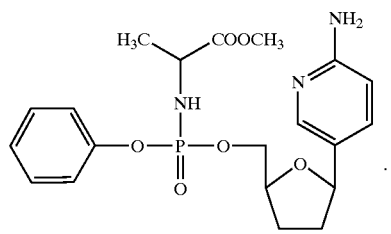

16. The method of claim 6 further comprising the step of:

vii) reacting the 5'-hydroxyl group with trimethylphosphate, phosphorous oxychloride and tetra-n-butylammonium pyrophosphate.

17. The method of claim 16 wherein the product compound is represented by the formula:

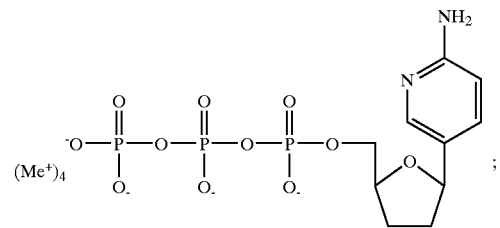

wherein the term Me$^+$ is defined to be a pharmaceutically acceptable monocation.

* * * * *

UNITED STATES PATENT AND TRADEMARK OFFICE
CERTIFICATE OF CORRECTION

PATENT NO.       : 6,914,052 B2
APPLICATION NO.  : 10/097672
DATED            : July 5, 2005
INVENTOR(S)      : McLaughlin et al.

It is certified that error appears in the above-identified patent and that said Letters Patent is hereby corrected as shown below:

COLUMN 23-24 CLAIM 1, should read as follows:

1. A compound of the formula:

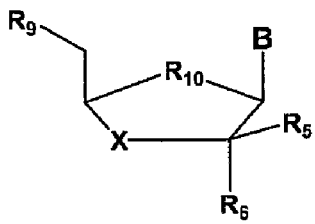

Wherein B =

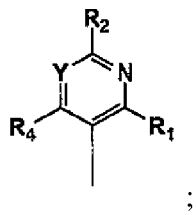

;

X represents $CR_7R_8$;

Y represents $CR_3$, or N;

$R_1$ represents H, F, Cl, Br, I, $CH_3$, or $CF_3$;

$R_2$ represents NHR wherein R is H, lower straight or branched chain alkyl, alkenyl of alkynyl consisting of 1 to 6 carbons;

$R_3$ is H, lower straight of branched chain alkyl, alkenyl of alkynyl consisting of 1 to 6 carbons, F, Cl, Br, or I;

$R_5$ is H, F, or OH;

$R_6$ is H, F, or OH;

with the proviso that when either of $R_5$ and $R_6$ is OH, then $R_6$ or $R_5$, respectively, cannot be either OH of F;

$R_7$ and $R_8$ independently represent H;

UNITED STATES PATENT AND TRADEMARK OFFICE
CERTIFICATE OF CORRECTION

PATENT NO. : 6,914,052 B2
APPLICATION NO. : 10/097672
DATED : July 5, 2005
INVENTOR(S) : McLaughlin et al.

It is certified that error appears in the above-identified patent and that said Letters Patent is hereby corrected as shown below:

COLUMN 23-24 CLAIM 1, should read as follows: (cont'd)

$R_9$ is OH or 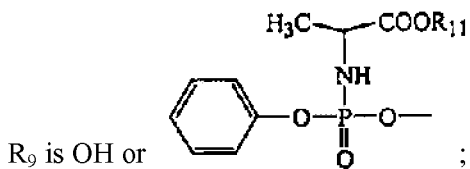 ;

wherein $R_{11}$ is straight of branched alkyl; and $R_{10}$ represents $CH_2$, O, S, or 5' triphosphate derivative thereof, pharmaceutically acceptable complex or a pharmaceutically acceptable salt thereof.

COLUMN 24-25 CLAIM 2, should read as follows:

2. A compound of Claim 1 wherein

B = 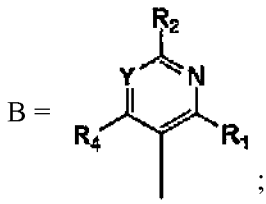 ;

X is $CR_7R_8$;

Y is $CR_3$;

$R_1$, $R_3$, $R_4$, $R_5$, $R_6$, $R_7$ and $R_8$ are H;

$R_2$ is $NH_2$;

UNITED STATES PATENT AND TRADEMARK OFFICE
CERTIFICATE OF CORRECTION

PATENT NO. : 6,914,052 B2
APPLICATION NO. : 10/097672
DATED : July 5, 2005
INVENTOR(S) : McLaughlin et al.

It is certified that error appears in the above-identified patent and that said Letters Patent is hereby corrected as shown below:

<u>COLUMN 26 CLAIM 11, should read as follows:</u>

11. A compound of the formula:

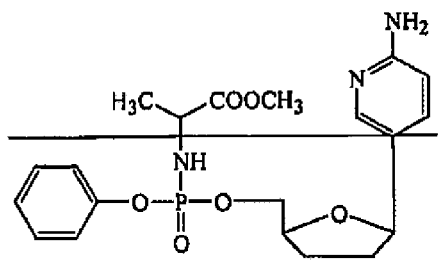 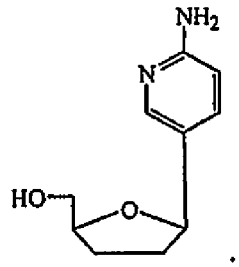

Signed and Sealed this

Seventh Day of August, 2007

JON W. DUDAS
*Director of the United States Patent and Trademark Office*

```
                            SEQUENCE LISTING

<160> NUMBER OF SEQ ID NOS: 3

<210> SEQ ID NO 1
<211> LENGTH: 23
<212> TYPE: DNA
<213> ORGANISM: Human immunodeficiency virus

<400> SEQUENCE: 1
caataggaac ccatgtaccg taa                                              23

<210> SEQ ID NO 2
<211> LENGTH: 24
<212> TYPE: DNA
<213> ORGANISM: Artificial Sequence
<220> FEATURE:
<223> OTHER INFORMATION: HIV with modified residue
<220> FEATURE:
<221> NAME/KEY: misc_feature
<222> LOCATION: (24)..(24)
<223> OTHER INFORMATION: 2-amino-5-(2',3'-dideoxy-beta-D-ribofuranosyl
      pyridine

<400> SEQUENCE: 2
caataggaac ccatgtaccg taan                                             24

<210> SEQ ID NO 3
<211> LENGTH: 30
<212> TYPE: DNA
<213> ORGANISM: Human immunodeficiency virus

<400> SEQUENCE: 3
gttatccttg ggtacatggc attgtcactc                                       30
```